(12) United States Patent
Koh et al.

(10) Patent No.: US 10,507,001 B2
(45) Date of Patent: Dec. 17, 2019

(54) X-RAY APPARATUS AND X-RAY SYSTEM

(71) Applicant: Samsung Electronics Co., Ltd., Gyeonggi-do (KR)

(72) Inventors: Byoung-hoon Koh, Seongnam-si (KR); Woo-sup Han, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 276 days.

(21) Appl. No.: 15/529,473

(22) PCT Filed: Nov. 23, 2015

(86) PCT No.: PCT/KR2015/012582
§ 371 (c)(1),
(2) Date: May 24, 2017

(87) PCT Pub. No.: WO2016/085211
PCT Pub. Date: Jun. 2, 2016

(65) Prior Publication Data
US 2017/0258434 A1    Sep. 14, 2017

(30) Foreign Application Priority Data
Nov. 24, 2014   (KR) .......................... 10-2014-0164417

(51) Int. Cl.
*A61B 6/00* (2006.01)
*G01T 7/00* (2006.01)

(52) U.S. Cl.
CPC .............. *A61B 6/54* (2013.01); *A61B 6/4291* (2013.01); *A61B 6/4464* (2013.01); *A61B 6/5258* (2013.01); *A61B 6/588* (2013.01); *G01T 7/00* (2013.01)

(58) Field of Classification Search
None
See application file for complete search history.

(56) References Cited

U.S. PATENT DOCUMENTS

| 6,447,164 | B1 | 9/2002 | Polkus |
| 8,340,241 | B2 | 12/2012 | Adachi et al. |
| 2002/0006185 | A1 | 1/2002 | Lienard et al. |
| 2005/0152502 | A1 | 7/2005 | Saunders et al. |
| 2006/0002513 | A1 | 1/2006 | Bernhardt et al. |
| 2006/0113481 | A1 | 6/2006 | Murphy et al. |
| 2010/0217161 | A1 | 8/2010 | Shalgi et al. |

(Continued)

FOREIGN PATENT DOCUMENTS

| JP | 2002000589 A | 1/2002 |
| JP | 2004081331 A | 3/2004 |

(Continued)

OTHER PUBLICATIONS

European Patent Office, "Supplementary European Search Report," Application No. EP 15 86 3610.0, dated Nov. 29, 2017, 7 pages.

*Primary Examiner* — Hoon K Song

(57) ABSTRACT

An X-ray apparatus includes an X-ray radiator configured to radiate X-rays, a controller that obtains arrangement information that indicates an arrangement status of the X-ray radiator and a detection device, and quality information that indicates the quality of an X-ray image, which corresponds to the arrangement status, and an output unit that outputs the arrangement information and the quality information.

19 Claims, 12 Drawing Sheets

(56) References Cited

U.S. PATENT DOCUMENTS

| | | | |
|---|---|---|---|
| 2011/0013747 A1* | 1/2011 | Banckwitz | A61B 6/4233 378/98 |
| 2011/0249793 A1 | 10/2011 | Lalena et al. | |
| 2011/0311026 A1 | 12/2011 | Lalena | |
| 2012/0230473 A1 | 9/2012 | Stagnitto et al. | |
| 2013/0051528 A1 | 2/2013 | Inglese et al. | |

FOREIGN PATENT DOCUMENTS

| | | |
|---|---|---|
| JP | 2004508086 A | 3/2004 |
| JP | 2007252898 A | 10/2007 |

* cited by examiner

[Fig. 4]
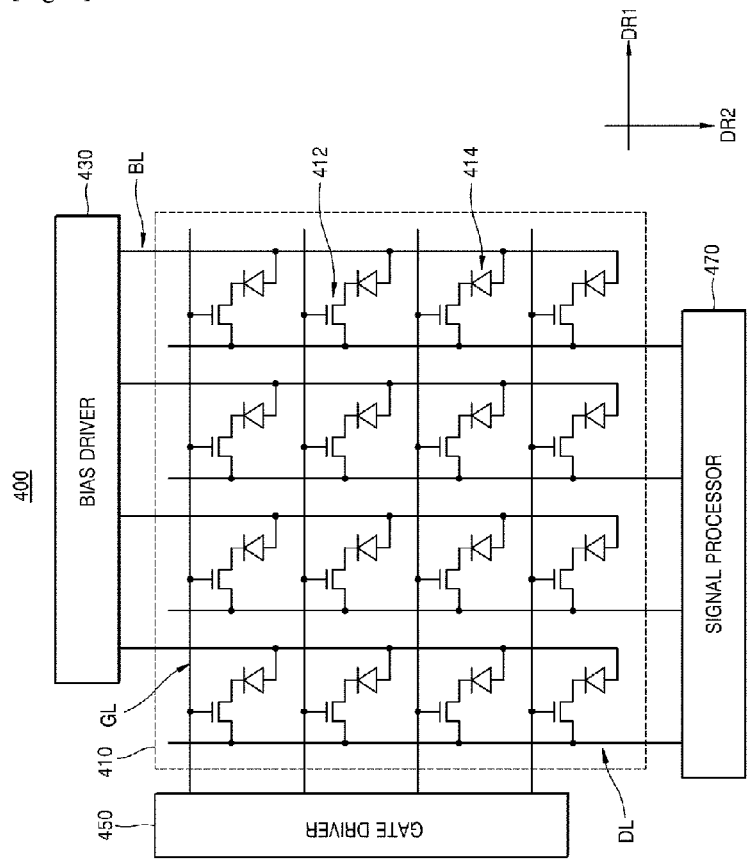
[Fig. 5]
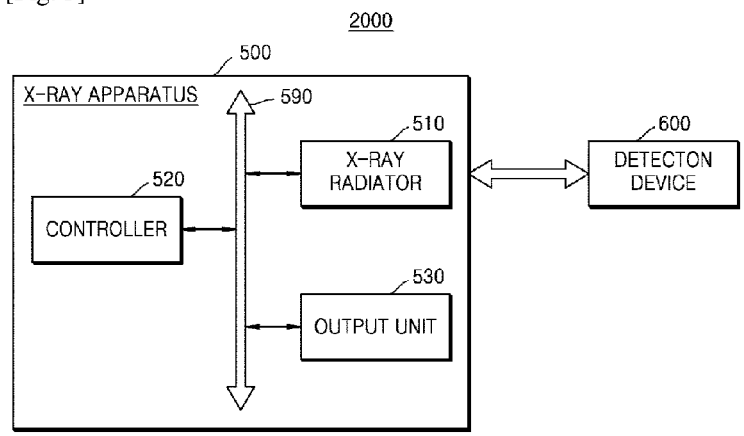
[Fig. 6]
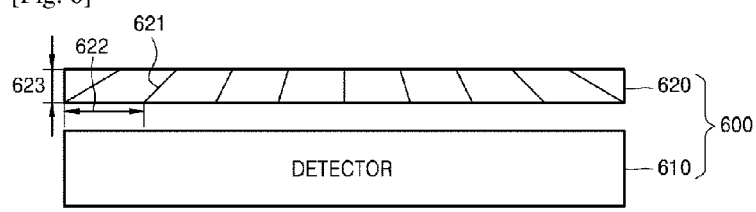

[Fig. 7]
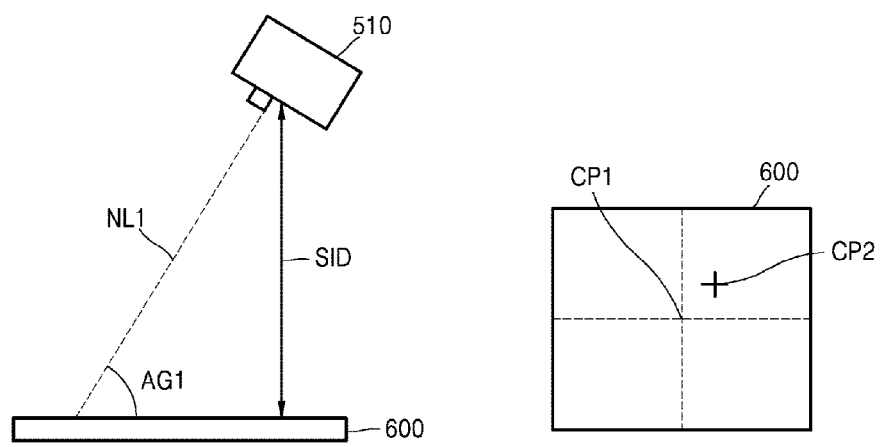
[Fig. 8]
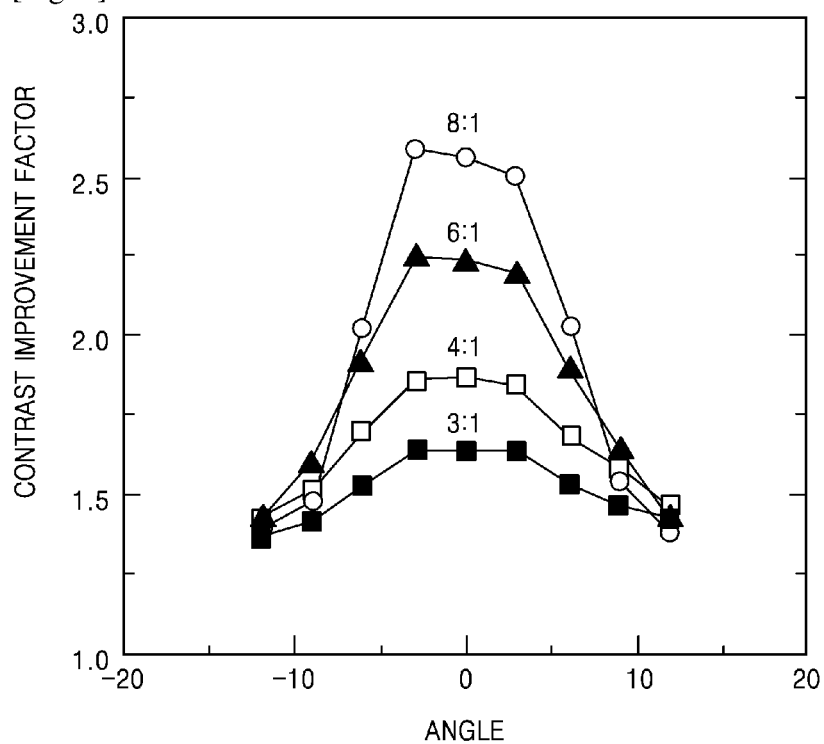

[Fig. 9]
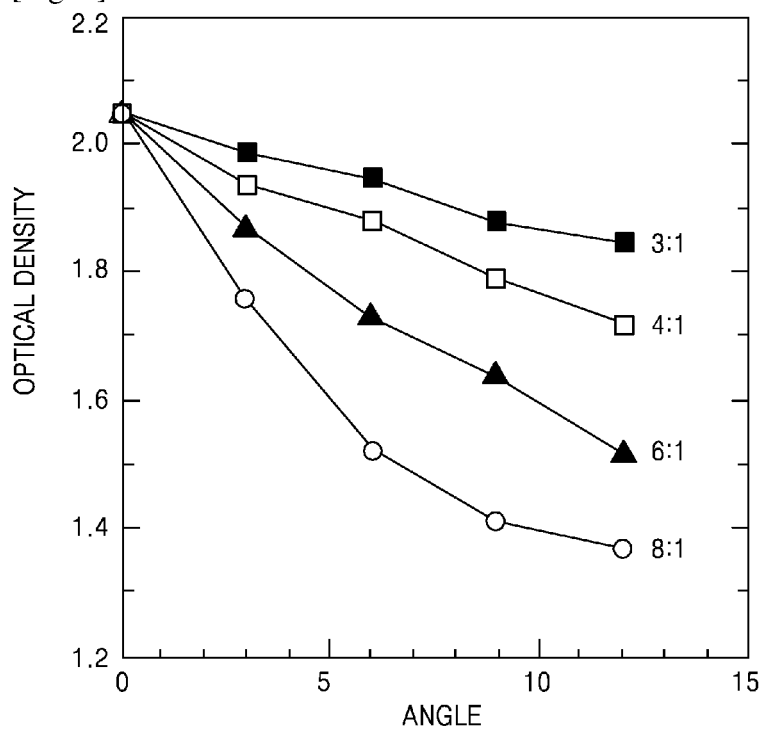
[Fig. 10]
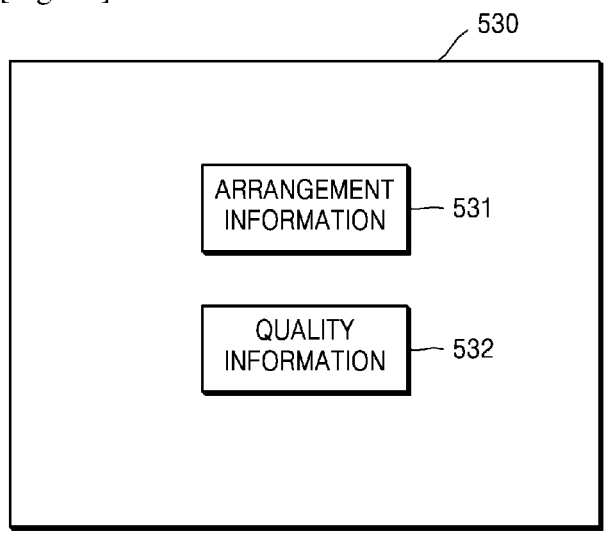

[Fig. 11]
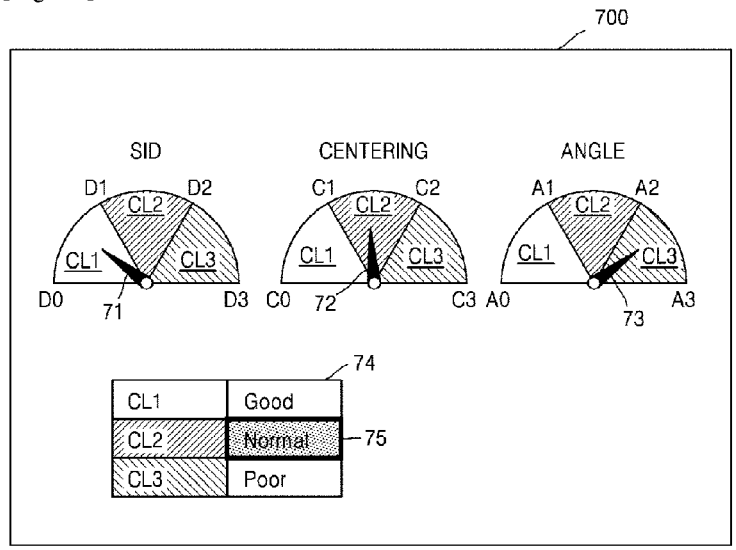
[Fig. 12]
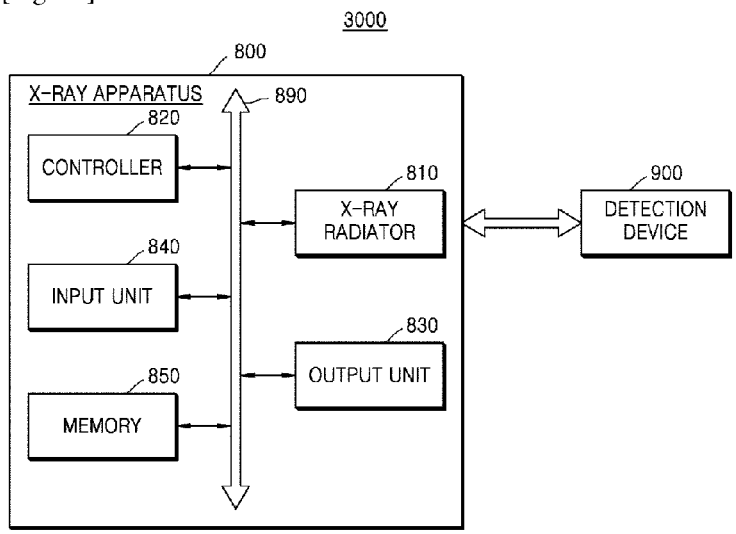
[Fig. 13]
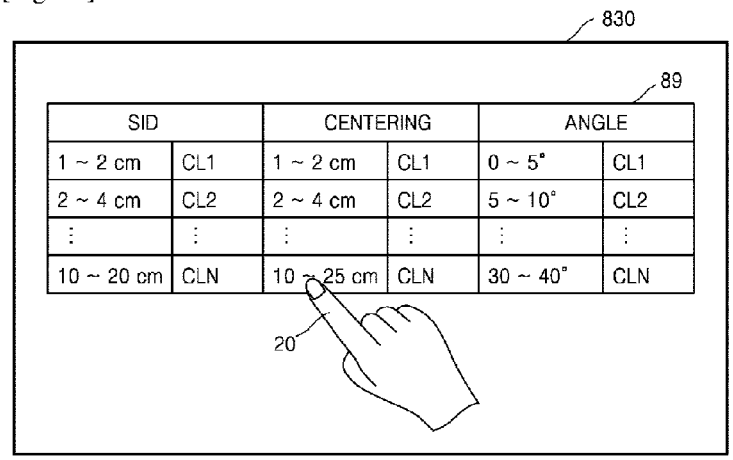

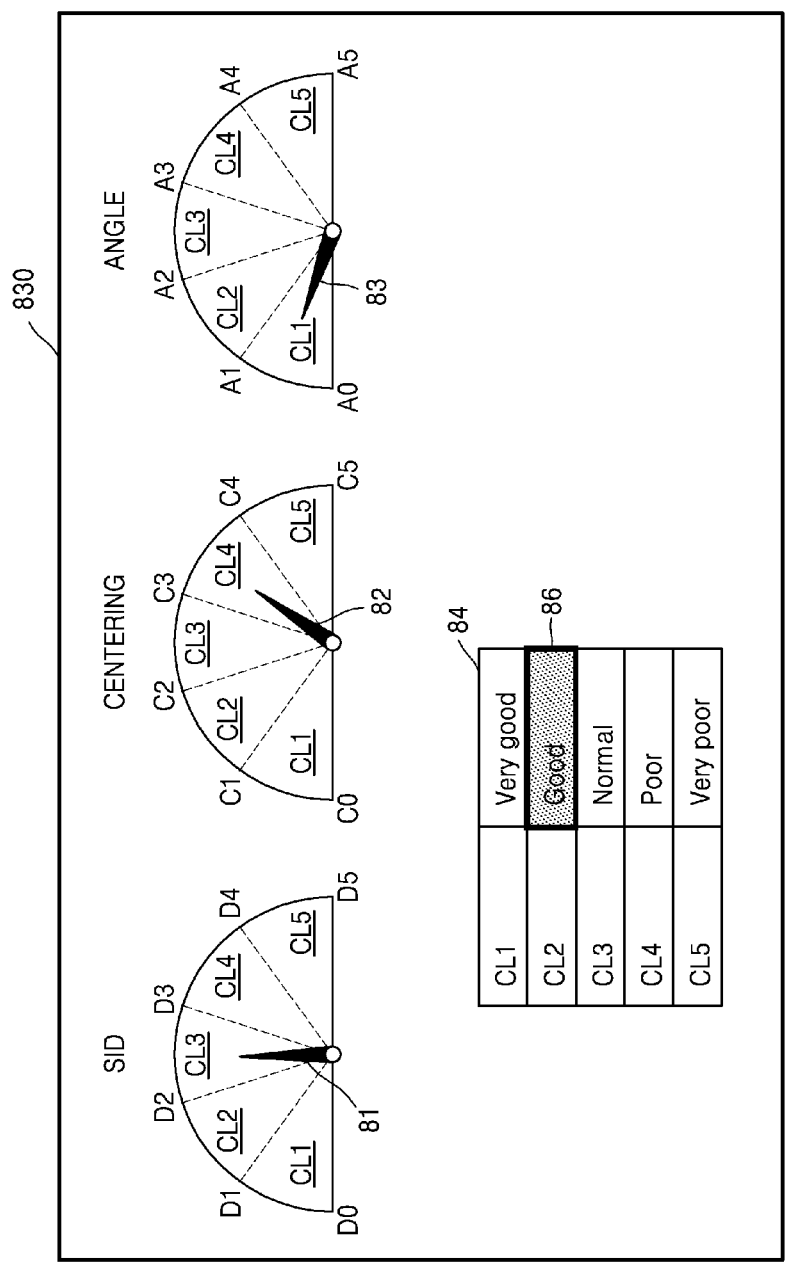
[Fig. 14]

[Fig. 15]
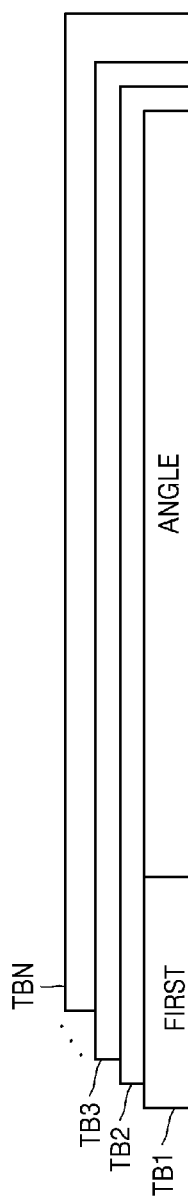

[Fig. 16]
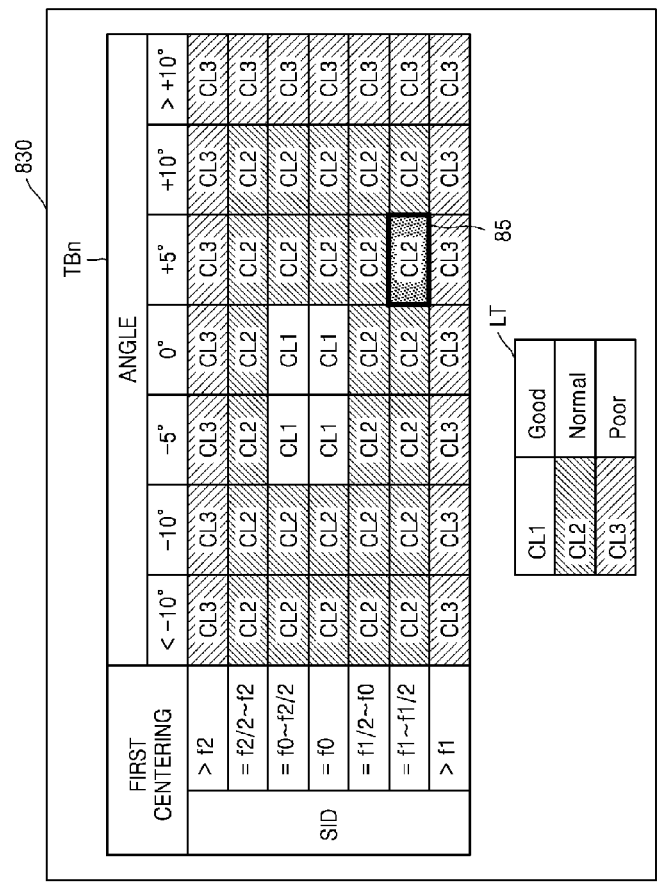
[Fig. 17]
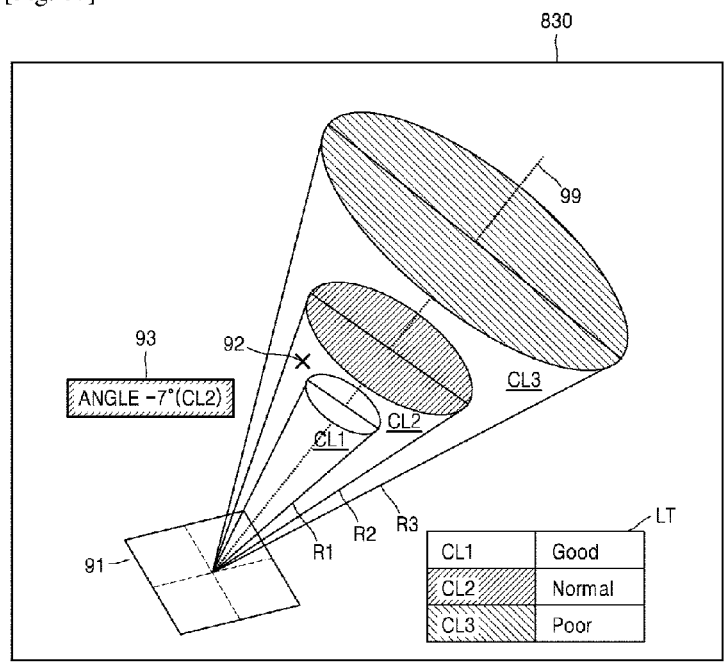

[Fig. 18]
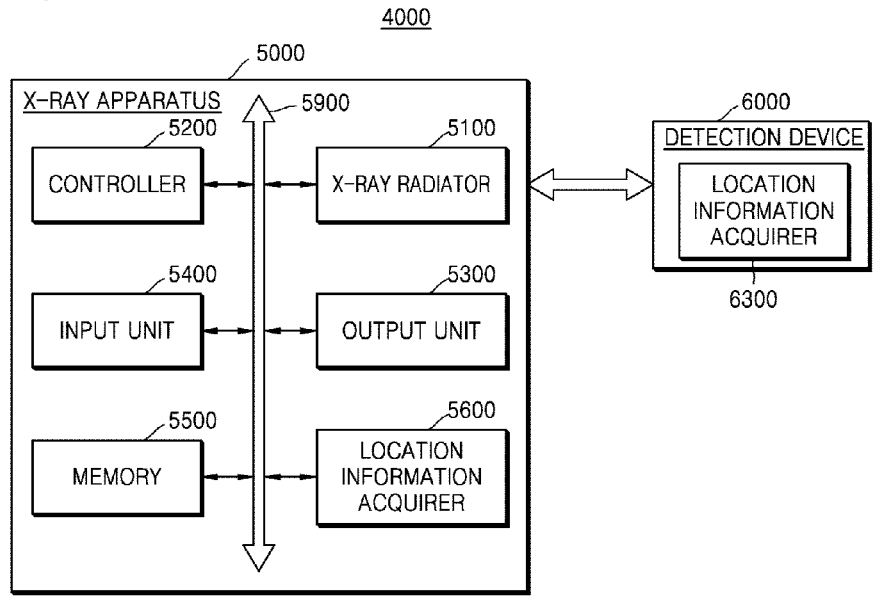
[Fig. 19]
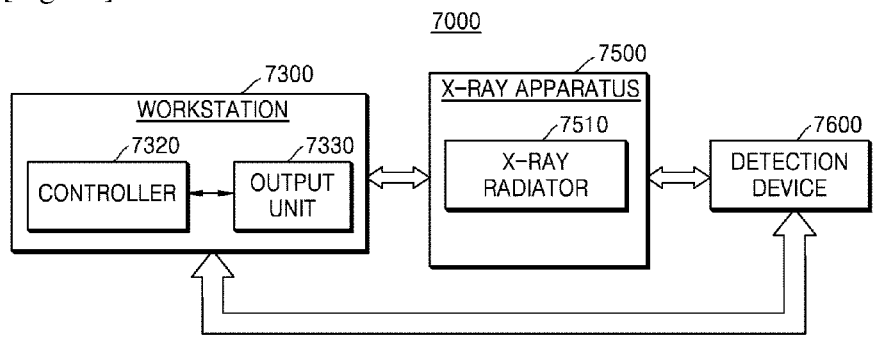
[Fig. 20]
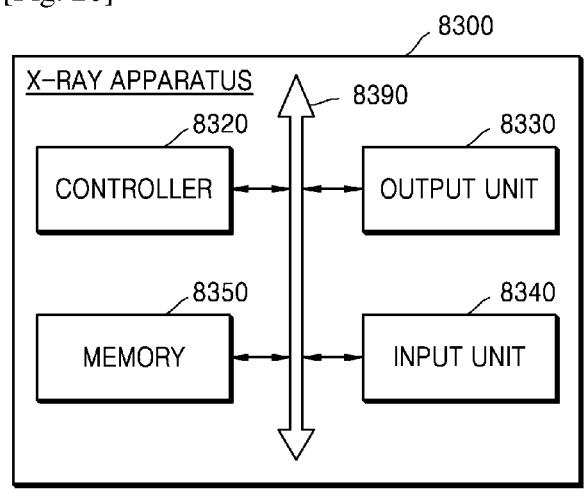

[Fig. 21]
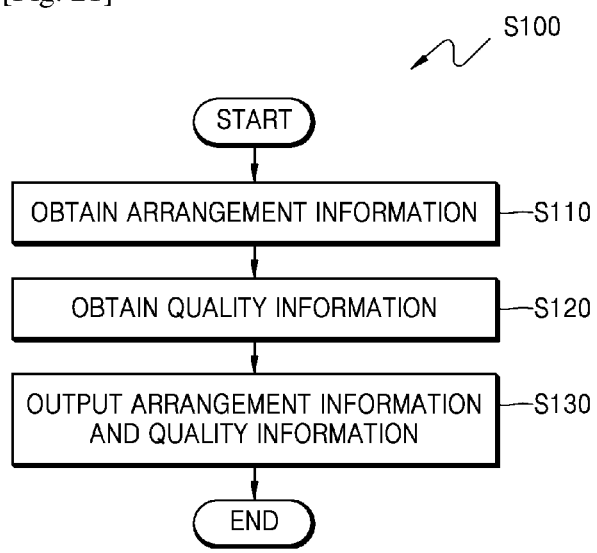

X-RAY APPARATUS AND X-RAY SYSTEM

CROSS-REFERENCE TO RELATED APPLICATION(S)

The present application claims priority under 35 U.S.C. § 365 to International Patent Application No. PCT/KR2015/012582 filed Nov. 23, 2015, entitled "X-RAY APPARATUS AND X-RAY SYSTEM", and, through International Patent Application No. PCT/KR2015/012582, to Korean Patent Application No. 10-2014-0164417 filed Nov. 24, 2014, each of which are incorporated herein by reference into the present disclosure as if fully set forth herein.

TECHNICAL FIELD

The present disclosure relates to an X-ray apparatus and an X-ray system, and more particularly, to an X-ray apparatus and an X-ray system in which a user may easily recognize an arrangement status of an X-ray radiator and a detection device and quality of an X-ray image.

BACKGROUND

X-rays are generally electromagnetic waves having wavelengths ranging from 0.01 Angstrom (Å) to about 100 Å Since X-rays may transmit through objects, X-rays may be widely used for medical apparatuses capturing images of inside of bodies or non-invasive examination apparatuses in general industries.

An X-ray apparatus that uses X-rays may obtain an X-ray image of an object by transmitting X-rays emitted from an X-ray source through an object, and detecting a difference between intensities of the transmitted X-rays by using an X-ray detector. The X-ray image may be used to understand an inner structure of the object and diagnose the object. By using the X-ray apparatus, the inner structure of the object may be easily understood based on a principle that the transmittance of X-rays varies according to the density of the object and atomic numbers of atoms that form the object. When wavelengths of X-rays are short, transmittance increases and a screen becomes brighter.

SUMMARY

According to an aspect of an exemplary embodiment, an X-ray apparatus includes an X-ray radiator configured to radiate X-rays, a controller that obtains arrangement information that indicates an arrangement status of the X-ray radiator and a detection device, and quality information that indicates the quality of an X-ray image, which corresponds to the arrangement status, and an output unit that outputs the arrangement information and the quality information.

Provided are an X-ray apparatus and a system in which a user may easily recognize an arrangement status of an X-ray radiator and a detection device and quality of an X-ray image.

BRIEF DESCRIPTION OF THE DRAWINGS

These and/or other aspects will become apparent and more readily appreciated from the following description of the exemplary embodiments, taken in conjunction with the accompanying drawings in which:

FIG. 4 is a schematic diagram showing a detailed configuration of a detector;

FIG. 5 is a block diagram of an X-ray system, according to some exemplary embodiments;

FIG. 6 is a diagram of a detection device of FIG. 5, according to some exemplary embodiments;

FIG. 7 is a diagram of an arrangement status of an X-ray radiator and a detection device of FIG. 5, according to some exemplary embodiments;

FIGS. 8 and 9 are exemplary graphs showing the quality of an X-ray image according to parallelness of an X-ray radiator and a detection device;

FIG. 10 is a diagram of an output unit of FIG. 5, according to some exemplary embodiments;

FIG. 11 is a diagram of an output unit, according to some exemplary embodiments;

FIG. 12 is a block diagram of an X-ray system, according to some exemplary embodiments;

FIG. 13 is a diagram of a user interface (UI) that is output by an output unit of FIG. 12, according to some exemplary embodiments;

FIG. 14 is a diagram of an output unit of FIG. 12, according to some exemplary embodiments;

FIG. 15 is a diagram of relationship information stored in a memory of FIG. 12, according to some exemplary embodiments;

FIG. 16 is a diagram of an output unit of FIG. 12, according to some exemplary embodiments;

FIG. 17 is a diagram of an output unit of FIG. 12, according to some exemplary embodiments;

FIG. 18 is a block diagram of an X-ray system, according to some exemplary embodiments;

FIG. 19 is a block diagram of an X-ray system, according to some exemplary embodiments;

FIG. 20 is a block diagram of a workstation, according to some exemplary embodiments; and FIG. 21 is a flowchart of a method of operating an X-ray system, according to some exemplary embodiments.

DETAILED DESCRIPTION

Figure 1:
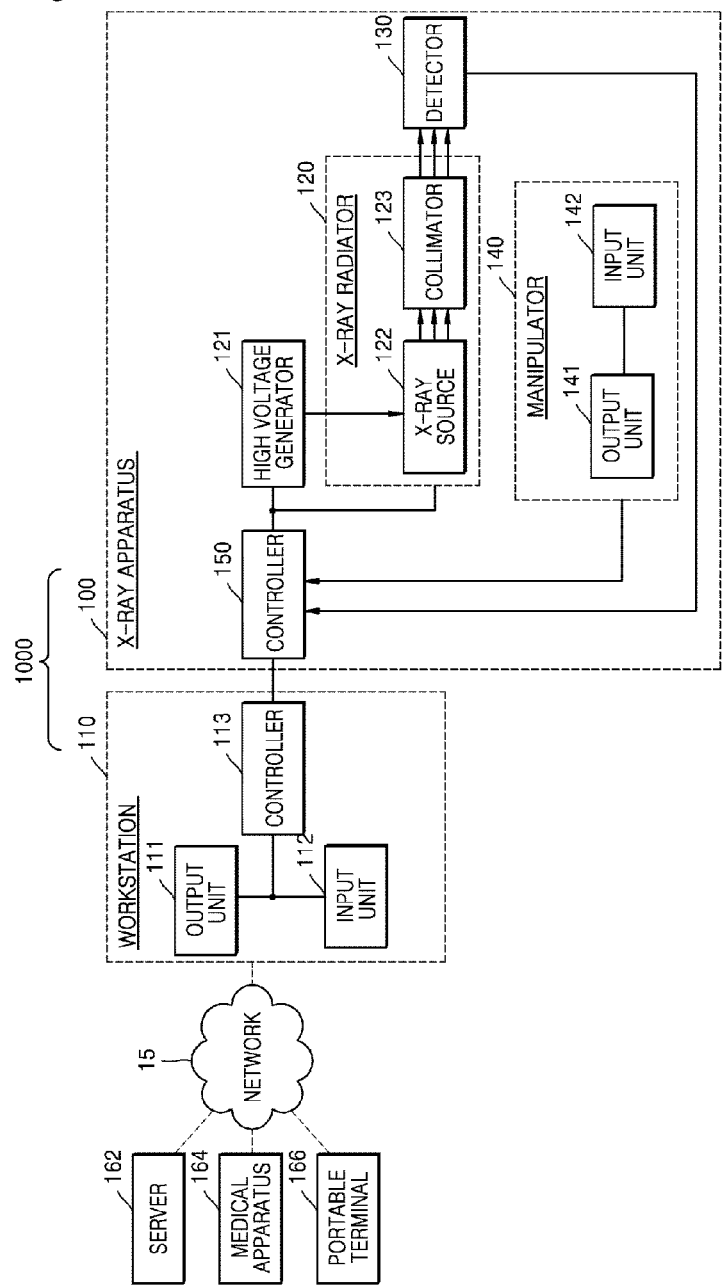
FIG. 1 is a block diagram of an X-ray system.

According to an aspect of an exemplary embodiment, an X-ray apparatus includes an X-ray radiator configured to radiate X-rays, a controller that obtains arrangement information that indicates an arrangement status of the X-ray radiator and a detection device, and quality information that indicates the quality of an X-ray image, which corresponds to the arrangement status, and an output unit that outputs the arrangement information and the quality information.

The output unit may further output relationship information that indicates qualities of an X-ray image, which respectively correspond to a plurality of arrangement ranges formable between the X-ray radiator and the detection device.

The arrangement information that is output from the output unit may indicate, on the relationship information, in which arrangement range from among the plurality of the arrangement ranges the arrangement status is included.

The output unit may output the relationship information such that the qualities of the X-ray image, which respectively correspond to the plurality of arrangement ranges, are distinguished from each other by using different colors.

The X-ray apparatus may further includes an input unit that receives, from a user, a command for setting or resetting the relationship information. The command for setting or re-setting the relationship information may include at least one selected from a command for setting or re-setting the plurality of arrangement ranges, a command for setting or re-setting the qualities of the X-ray image, which respectively correspond to the plurality of arrangement ranges, and a command for setting or re-setting colors that distinguishes the qualities of the X-ray image, which respectively correspond to the plurality of arrangement ranges, from each other.

The X-ray apparatus may further include an input unit that receives, from a user, at least one selected from an adjustment command for adjusting a location of at least one of the X-ray radiator and the detection device, and a radiation command for instructing the X-ray radiator to radiate X-rays. The controller controls an operation of at least one of the X-ray radiator and the detection device, based on the adjustment command or the radiation command.

The X-ray apparatus may further include a memory that stores the relationship information.

The X-ray apparatus may further include a location information acquirer that obtains location information of at least one of the X-ray radiator and the detection device, and the controller obtains the arrangement information based on the location information.

The arrangement information may include at least one selected from angle information that indicates parallelness of the X-ray radiator and the detection device, centering information that indicates a degree of matching between a center of the X-ray radiator and a center of the detection device, and distance information about a distance between the X-ray radiator and the detection device.

The detection device may include a grid configured to selectively transmit X-rays radiated from the X-ray radiator, and a detector that detects the X-rays transmitted through the grid.

According to an aspect of another exemplary embodiment, a workstation includes a controller that obtains arrangement information that indicates an arrangement status of an X-ray radiator of an X-ray apparatus and a detection device, and obtains quality information that indicates the quality of an X-ray image, which corresponds to the arrangement status, and an output unit that outputs the arrangement information and the quality information.

The output unit may further output relationship information that indicates qualities of an X-ray image, which respectively correspond to a plurality of arrangement ranges formable between the X-ray radiator and the detection device.

The arrangement information that is output from the output unit may indicate, on the relationship information, in which arrangement range from among the plurality of the arrangement ranges the arrangement status is included.

The output unit may output the relationship information such that the qualities of the X-ray image, which respectively correspond to the plurality of arrangement ranges, are distinguished from each other by using different colors.

The workstation may further include an input unit that receives, from a user, a command for setting or re-setting the relationship information. The command for setting or re-setting the relationship information may include at least one selected from a command for setting or re-setting the plurality of arrangement ranges, a command for setting or re-setting the qualities of the X-ray image, which respectively correspond to the plurality of arrangement ranges, and a command for setting or re-setting colors that distinguishes the qualities of the X-ray image, which respectively correspond to the plurality of arrangement ranges, from each other.

The workstation may further include an input unit that receives, from a user, at least one selected from an adjustment command for adjusting a location of at least one of the X-ray radiator and the detection device, and a radiation command for instructing the X-ray radiator to radiate X-rays. The controller controls an operation of at least one of the X-ray radiator and the detection device, based on the adjustment command or the radiation command.

According to an aspect of another exemplary embodiment, a method of operating an X-ray system includes obtaining arrangement information that indicates an arrangement status of an X-ray radiator of an X-ray apparatus and a detection device, obtaining quality information that indicates the quality of an X-ray image, which corresponds to the arrangement status, and outputting the arrangement information and the quality information The arrangement information and the quality information may be output with relationship information that indicates qualities of an X-ray image, which respectively correspond to a plurality of arrangement ranges formable between the X-ray radiator and the detection device.

The method may further include receiving, from a user, at least one selected from an adjustment command for adjusting a location of at least one of the X-ray radiator and the detection device, and a radiation command for instructing the X-ray radiator to radiate X-rays, and controlling an operation of at least one of the X-ray radiator and the detection device, based on the adjustment command or the radiation command.

Additional aspects will be set forth in part in the description which follows and, in part, will be apparent from the description, or may be learned by practice of the presented exemplary embodiments.

The attached drawings for illustrating exemplary embodiments of the present disclosure are referred to in order to gain a sufficient understanding of the present disclosure, the merits thereof, and the objectives accomplished by the implementation of the present disclosure. The present disclosure may, however, be embodied in many different forms and should not be construed as being limited to the embodiments set forth herein; rather, these embodiments are provided such that this disclosure will be thorough and complete, and will fully convey the concept of the invention to one of ordinary skill in the art.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the specification should be understood not as simple names but based on the meaning of the terms and the overall description.

Throughout the specification, an "image" may denote multi-dimensional data composed of discrete image elements (for example, pixels in a 2-dimensional (2D) image and voxels in a 3-dimensional (3D) image). For example, an image may be a medical image of an object acquired by an X-ray apparatus, a computed tomography (CT) apparatus, a magnetic resonance imaging (MRI) apparatus, an ultrasound diagnosis apparatus, or another medical imaging apparatus.

In addition, an "object" may be a human, an animal, or a part of a human or animal. For example, the object may include an organ (for example, the liver, the heart, the womb, the brain, breasts, or the abdomen), blood vessels, or a combination thereof. The object may be a phantom. The phantom denotes a material having a volume, a density, and an effective atomic number that are approximately the same as those of a living organism. For example, the phantom may be a spherical phantom having similar properties to those of the human body.

Throughout the specification, a "user" may be, but is not limited to, a medical expert, for example, a medical doctor, a nurse, a medical laboratory technologist, or a medical imaging expert, or a technician who repairs medical apparatuses.

An X-ray apparatus is a medical imaging apparatus that acquires images of internal structures of an object by transmitting an X-ray through the human body. The X-ray apparatus may acquire medical images of an object more simply within a shorter time than other medical imaging apparatuses including an MRI apparatus and a CT apparatus. Therefore, the X-ray apparatus is widely used in simple chest imaging, simple abdomen imaging, simple skeleton imaging, simple nasal sinuses imaging, simple neck soft tissue imaging, and breast imaging.

FIG. 1 is a block diagram of an X-ray system 1000. Referring to FIG. 1, the X-ray system 1000 includes an X-ray apparatus 100 and a workstation 110. The X-ray apparatus 100 shown in FIG. 1 may be a fixed-type X-ray apparatus or a mobile X-ray apparatus. The X-ray apparatus 100 may include an X-ray radiator 120, a high voltage generator 121, a detector 130, a manipulator 140, and a controller 150. The controller 150 may control overall operations of the X-ray apparatus 100.

The high voltage generator 121 generates a high voltage for generating X-rays, and applies the high voltage to an X-ray source 122.

The X-ray radiator 120 includes the X-ray source 122 receiving the high voltage from the high voltage generator 121 to generate and radiate X-rays, and a collimator 123 for guiding a path of the X-ray radiated from the X-ray source 122 and adjusting an irradiation region radiated by the X-ray.

The X-ray source 122 includes an X-ray tube that may be realized as a vacuum tube diode including a cathode and an anode. An inside of the X-ray tube is set as a high vacuum state of about 10 mmHg, and a filament of the anode is heated to a high temperature to generate thermal electrons. The filament may be a tungsten filament, and a voltage of about 10 V and a current of about 3 Å to about 5 Å may be applied to an electric wire connected to the filament to heat the filament.

In addition, when a high voltage of about 10 kVp to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into the X-ray.

The cathode is mainly formed of copper, and the target material is located opposite to the anode. The target material may be a high resistive material such as chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased to be at least ten times greater than that of a case where the target material is fixed.

The voltage applied between the cathode and the anode of the X-ray tube is referred to as a tube voltage, and the tube voltage is applied from the high voltage generator 121 and a magnitude of the tube voltage may be expressed by a crest value (kVp). When the tube voltage increases, a velocity of the thermal electrons increases, and accordingly, energy of the X-ray (energy of photon) that is generated when the thermal electrons collide with the target material is increased. The current flowing in the X-ray tube is referred to as a tube current that may be expressed as an average value (mA). When the tube current increases, the number of thermal electrons emitted from the filament is increased, and accordingly, the X-ray dose (the number of X-ray photons) generated when the thermal electrons collide with the target material is increased.

Therefore, the energy of the X-ray may be adjusted according to the tube voltage, and the intensity of the X-ray or the X-ray dose may be adjusted according to the tube current and the X-ray exposure time.

The detector 130 detects an X-ray that is radiated from the X-ray radiator 120 and has been transmitted through an object. The detector 130 may be a digital detector. The detector 130 may be implemented by using a thin film transistor (TFT) or a charge coupled device (CCD). Although the detector 130 is included in the X-ray apparatus 100 in FIG. 1, the detector 130 may be an X-ray detector that is a separate device capable of being connected to or separated from the X-ray apparatus 100.

The X-ray apparatus 100 may further include the manipulator 140 for providing a user with an interface for manipulating the X-ray apparatus 100. The manipulator 140 may include an output unit 141 and an input unit 142. The input unit 142 may receive from a user a command for manipulating the X-ray apparatus 100 and various types of information related to X-ray imaging. The controller 150 may control or manipulate the X-ray apparatus 100 according to the information received by the input unit 142. The output unit 141 may output sound representing information related to a imaging operation such as the X-ray radiation under the control of the controller 150.

The workstation 110 and the X-ray apparatus 100 may be connected to each other by wire or wirelessly. When they are connected to each other wirelessly, a device (not shown) for synchronizing clock signals with each other may be further included. The workstation 110 and the X-ray apparatus 100 may exist within physically separate spaces.

The workstation 110 may include an output unit 111, an input unit 112, and a controller 113. The output unit 111 and the input unit 112 provide a user with an interface for manipulating the workstation 110 and the X-ray apparatus 100. The controller 113 may control the workstation 110 and the X-ray apparatus 100.

The X-ray apparatus 100 may be controlled via the workstation 110 or may be controlled by the controller 150 included in the X-ray apparatus 100. Accordingly, a user may control the X-ray apparatus 100 via the workstation 110 or may control the X-ray apparatus 100 via the manipulator 140 and the controller 150 included in the X-ray apparatus 100. In other words, a user may remotely control the X-ray apparatus 100 via the workstation 110 or may directly control the X-ray apparatus 100.

Although the controller 113 of the workstation 110 is separate from the controller 150 of the X-ray apparatus 100 in FIG. 1, FIG. 1 is only an example. As another example, the controllers 113 and 150 may be integrated into a single controller, and the single controller may be included in only one of the workstation 110 and the X-ray apparatus 100. Hereinafter, the controllers 113 and 150 may denote the controller 113 of the workstation 110 and/or the controller 150 of the X-ray apparatus 100.

The output unit 111 and the input unit 112 of the workstation 110 may provide a user with an interface for manipulating the X-ray apparatus 100, and the output unit 141 and the input unit 142 of the X-ray apparatus 100 may also provide a user with an interface for manipulating the X-ray apparatus 100. Although the workstation 110 and the X-ray radiation apparatus 100 include the output units 111 and 141, respectively, and the input units 112 and 142, respectively, in FIG. 1, embodiments are not limited thereto. Only one of the workstation 110 and the X-ray apparatus 100 may include an output unit or an input unit.

Hereinafter, the input units 112 and 142 may denote the input unit 112 of the workstation 110 and/or the input unit 142 of the X-ray apparatus 100, and the output units 111 and 141 may denote the output unit 111 of the workstation 110 and/or the output unit 141 of the X-ray apparatus 100.

Examples of the input units 112 and 142 may include a keyboard, a mouse, a touch screen, a voice recognizer, a fingerprint recognizer, an iris recognizer, and other input devices which are well known to one of ordinary skill in the art. The user may input a command for radiating the X-ray via the input units 112 and 142, and the input units 112 and 142 may include a switch for inputting the command. The switch may be configured so that a radiation command for radiating the X-ray may be input only when the switch is pushed twice.

In other words, when the user pushes the switch, a prepare command for performing a pre-heating operation for X-ray radiation may be input through the switch, and then, when the user pushes the switch once more, the radiation command for performing substantial X-ray radiation may be input through the switch. When the user manipulates the switch as described above, the controllers 113 and 150 generate signals corresponding to the commands input through the switch manipulation, that is, a prepare signal, and transmit the generated signals to the high voltage generator 121 generating a high voltage for generating the X-ray.

When the high voltage generator 121 receives the prepare signal from the controllers 113 and 150, the high voltage generator 121 starts a pre-heating operation, and when the pre-heating is finished, the high voltage generator 121 outputs a ready signal to the controllers 113 and 150. In addition, the detector 130 also needs to prepare to detect the X-ray, and thus the high voltage generator 121 performs the pre-heating operation and the controllers 113 and 150 transmit a prepare signal to the detector 130 so that the detector 130 may prepare to detect the X-ray transmitted through the object. The detector 130 prepares to detect the X-ray in response to the prepare signal, and when the preparing for the detection is finished, the detector 130 outputs a ready signal to the controllers 113 and 150.

When the pre-heating operation of the high voltage generator 121 is finished and the detector 130 is ready to detect the X-ray, the controllers 113 and 150 transmit a radiation signal to the high voltage generator 121, the high voltage generator 121 generates and applies the high voltage to the X-ray source 122, and the X-ray source 122 radiates the X-ray.

When the controllers 113 and 150 transmit the radiation signal to the high voltage generator 121, the controllers 113 and 150 may transmit a sound output signal to the output units 111 and 141 so that the output units 111 and 141 output a predetermined sound and the object may recognize the radiation of the X-ray. The output units 111 and 141 may also output a sound representing information related to imaging in addition to the X-ray radiation. In FIG. 1, the output unit 141 is included in the manipulator 140; however, the embodiments are not limited thereto, and the output unit 141 or a portion of the output unit 141 may be located elsewhere. For example, the output unit 141 may be located on a wall of an examination room in which the X-ray imaging of the object is performed.

The controllers 113 and 150 control locations of the X-ray radiator 120 and the detector 130, imaging timing, and imaging conditions, according to imaging conditions set by the user.

In more detail, the controllers 113 and 150 control the high voltage generator 121 and the detector 130 according to the command input via the input units 112 and 142 so as to control radiation timing of the X-ray, an intensity of the X-ray, and a region radiated by the X-ray. In addition, the control units 113 and 150 adjust the location of the detector 130 according to a predetermined imaging condition, and control operation timing of the detector 130.

Furthermore, the controllers 113 and 150 generate a medical image of the object by using image data received via the detector 130. In detail, the controllers 113 and 150 may receive the image data from the detector 130, and then, generate the medical image of the object by removing noise from the image data and adjusting a dynamic range and interleaving of the image data.

The output units 111 and 141 may output the medical image generated by the controllers 113 and 150. The output units 111 and 141 may output information that is necessary for the user to manipulate the X-ray apparatus 100, for example, a user interface (UI), user information, or object information. Examples of the output units 111 and 141 may include a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a 3D display, a transparent display, and other various output devices well known to one of ordinary skill in the art.

The workstation 110 shown in FIG. 1 may further include a communicator (not shown) that may be connected to a server 162, a medical apparatus 164, and a portable terminal 166 via a network 15.

The communicator may be connected to the network 15 by wire or wirelessly to communicate with the server 162, the medical apparatus 164, or the portable terminal 166. The communicator may transmit or receive data related to diagnosis of the object via the network 15, and may also transmit or receive medical images captured by the medical apparatus 164, for example, a CT apparatus, an MRI apparatus, or an X-ray apparatus. Moreover, the communicator may receive a medical history or treatment schedule of an object (e.g., a patient) from the server 162 to diagnose a disease of the object. Also, the communicator may perform data communication with the portable terminal 166 such as a mobile phone, a personal digital assistant (PDA), or a laptop computer of a medical doctor or a client, as well as the server 162 or the medical apparatus 164 in a hospital.

The communicator may include one or more elements enabling communication with external apparatuses. For example, the communicator may include a local area communication module, a wired communication module, and a wireless communication module.

The local area communication module refers to a module for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and receives a wireless signal to and from at least one selected from a base station, an external apparatus, and a server in a mobile communication network. Here, examples of the wireless signal may include a voice call signal, a video call signal, and various types of data according to text/multimedia messages transmission.

The X-ray apparatus 100 shown in FIG. 1 may include a plurality of digital signal processors (DSPs), an ultra-small calculator, and a processing circuit for special purposes (for example, high speed analog/digital (A/D) conversion, high speed Fourier transformation, and an array process).

In addition, communication between the workstation 110 and the X-ray apparatus 100 may be performed using a high speed digital interface, such as low voltage differential signaling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 2:
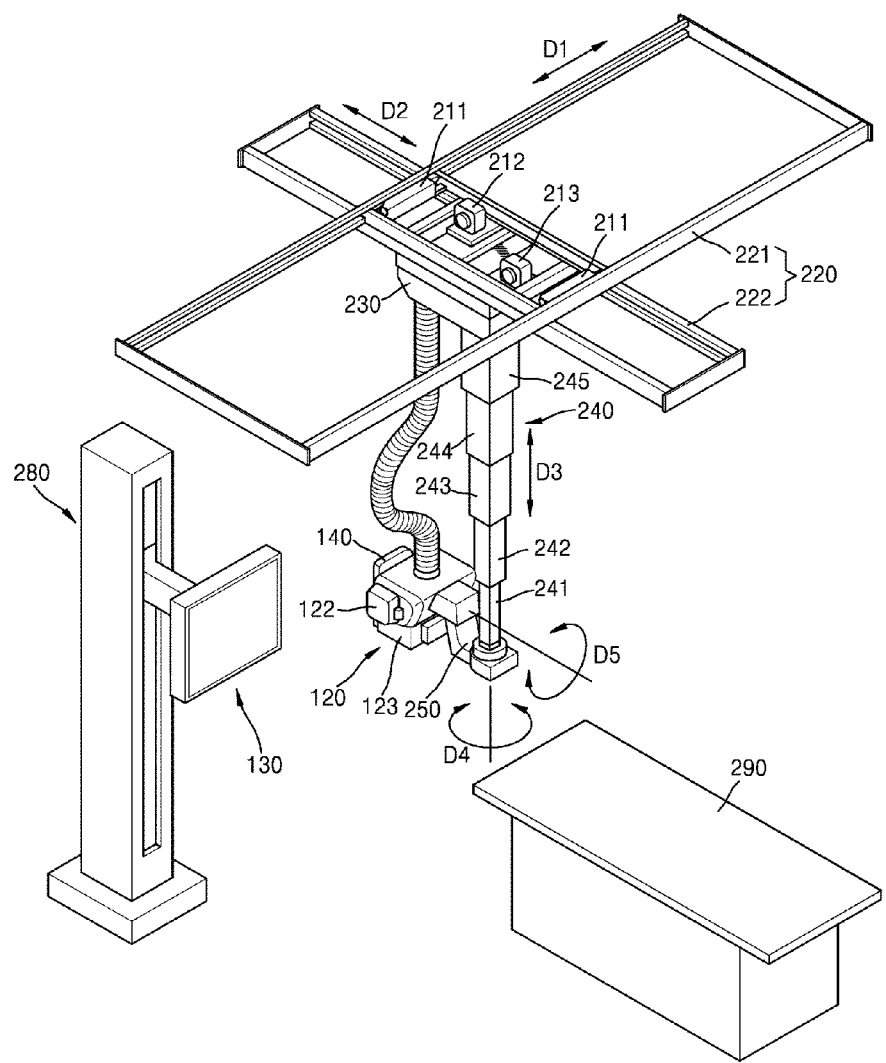
FIG. 2 is a perspective view of a fixed-type X-ray apparatus.

FIG. 2 is a perspective view of a fixed-type X-ray apparatus 200. The fixed-type X-ray apparatus 200 may be another embodiment of the X-ray apparatus 100 of FIG. 1. Components included in the fixed-type X-ray apparatus 200 that are the same as those of the X-ray apparatus 100 of FIG. 1 use the same reference numerals, and repeated descriptions thereof will be omitted.

Referring to FIG. 2, the fixed-type X-ray apparatus 200 includes a manipulator 140 providing a user with an interface for manipulating the X-ray apparatus 200, an X-ray radiator 120 radiating an X-ray to an object, a detector 130 detecting an X-ray that has passed through the object, first, second, and third motors 211, 212, and 213 providing a driving power to transport the X-ray radiator 120, a guide rail 220, a moving carriage 230, and a post frame 240. The guide rail 220, the moving carriage 230, and the post frame 240 are formed to transport the X-ray radiator 120 by using the driving power of the first, second, and third motors 211, 212, and 213.

The guide rail 220 includes a first guide rail 221 and a second guide rail 222 that are provided to form a predetermined angle with respect to each other. The first guide rail 221 and the second guide rail 222 may respectively extend in directions crossing each other at 90°.

The first guide rail 221 is provided on the ceiling of an examination room in which the fixed-type X-ray apparatus 200 is located.

The second guide rail 222 is located under the first guide rail 221, and is mounted so as to slide along the first guide rail 221. A roller (not shown) that may move along the first guide rail 221 may be provided on the first guide rail 221. The second guide rail 222 is connected to the roller to move along the first guide rail 221.

A first direction D1 is defined as a direction in which the first guide rail 221 extends, and a second direction D2 is defined as a direction in which the second guide rail 222 extends. Therefore, the first direction D1 and the second direction D2 cross each other at 90°, and may be parallel to the ceiling of the examination room.

The moving carriage 230 is located under the second guide rail 222 so as to move along the second guide rail 222. A roller (not shown) moving along the second guide rail 222 may be provided on the moving carriage 230.

Therefore, the moving carriage 230 may move in the first direction D1 together with the second guide rail 222, and may move in the second direction D2 along the second guide rail 222.

The post frame 240 is fixed on the moving carriage 230 and located under the moving carriage 230. The post frame 240 may include a plurality of posts 241, 242, 243, 244, and 245.

The plurality of posts 241, 242, 243, 244, and 245 are connected to each other to be foldable, and thus, the post frame 240 may have a length that is adjustable in a vertical direction of the examination room while in a state of being fixed to the moving carriage 230.

A third direction D3 is defined as a direction in which the length of the post frame 240 increases or decreases. Therefore, the third direction D3 may be perpendicular to the first direction D1 and the second direction D2.

The detector 130 detects the X-ray that has passed through the object, and may be combined with a table-type receptor 290 or a stand-type receptor 280.

A rotating joint 250 is located between the X-ray radiator 120 and the post frame 240. The rotating joint 250 allows the X-ray radiator 120 to be coupled to the post frame 240, and supports a load applied to the X-ray radiator 120.

The X-ray radiator 120 connected to the rotating joint 250 may rotate on a plane that is perpendicular to the third direction D3. In this case, a rotating direction of the X-ray radiator 120 may be defined as a fourth direction D4.

Also, the X-ray radiator 120 may be configured to be rotatable on a plane perpendicular to the ceiling of the examination room. Therefore, the X-ray radiator 120 may rotate in a fifth direction D5 that is a rotating direction about an axis that is parallel with the first direction D1 or the second direction D2, with respect to the rotating joint 250.

The first, second, and third motors 211, 212, and 213 may be provided to move the X-ray radiator 120 in the first, second, and third directions D1, D2, and D3. The first, second, and third motors 211, 212, and 213 may be electrically driven, and the first, second, and third motors 211, 212, and 213 may respectively include an encoder.

The first, second, and third motors 211, 212, and 213 may be located at various locations in consideration of design convenience. For example, the first motor 211, moving the second guide rail 222 in the first direction D1, may be located around the first guide rail 221, the second motor 212, moving the moving carriage 230 in the second direction D2, may be located around the second guide rail 222, and the third motor 213, increasing or reducing the length of the post frame 240 in the third direction D3, may be located in the moving carriage 230. In another example, the first, second, and third motors 211, 212, and 213 may be connected to a power transfer unit (not shown) so as to linearly move the X-ray radiator 120 in the first, second, and third directions D1, D2, and D3. The driving power transfer unit may be a combination of a belt and a pulley, a combination of a chain and a sprocket, or a shaft, which are generally used.

In another example, motors (not shown) may be located between the rotating joint 250 and the post frame 240 and between the rotating joint 250 and the X-ray radiator 120 in order to rotate the X-ray radiator 120 in the fourth and fifth directions D4 and D5.

The manipulator 140 may be located on a side surface of the X-ray radiator 120.

Although FIG. 2 shows the fixed-type X-ray apparatus 200 connected to the ceiling of the examination room, the fixed-type X-ray apparatus 200 is merely an example for convenience of comprehension. That is, X-ray apparatuses according to embodiments of the present disclosure may include X-ray apparatuses having various structures that are well known to one of ordinary skill in the art, for example, a C-arm-type X-ray apparatus and an angiography X-ray apparatus, in addition to the fixed-type X-ray apparatus 200 of FIG. 2.

Figure 3:
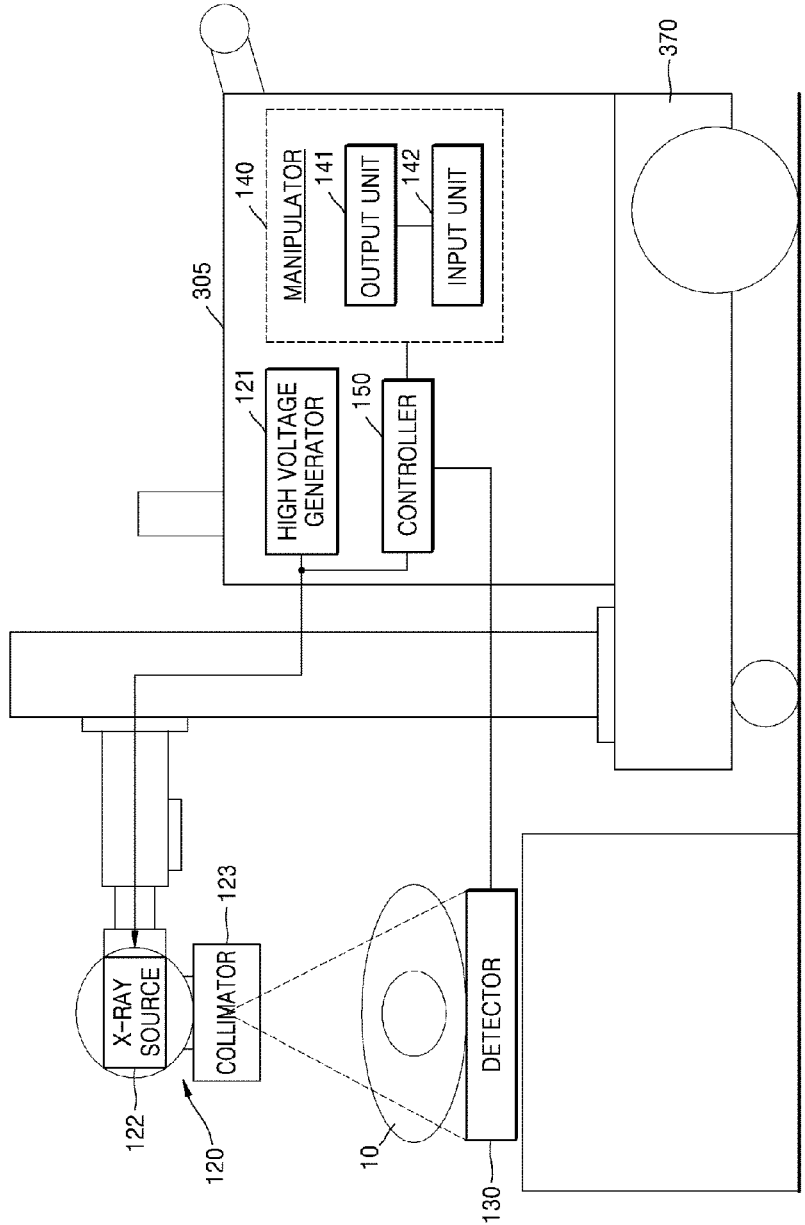
FIG. 3 is a diagram showing a configuration of a mobile X-ray apparatus.

FIG. 3 is a diagram showing a configuration of a mobile X-ray apparatus 300 capable of performing an X-ray imaging operation regardless of a place where the imaging operation is performed. The mobile X-ray apparatus 300 may be another embodiment of the X-ray apparatus 100 of FIG. 1. Components included in the mobile X-ray apparatus 300 that are the same as those of the X-ray apparatus 100 of FIG. 1 use the same reference numerals as those used in FIG. 1, and repeated descriptions thereof will be omitted.

Referring to FIG. 3, the mobile X-ray apparatus 300 includes a transport unit 370 including a wheel for transporting the mobile X-ray apparatus 300, a main unit 305, an X-ray radiator 120, and a detector 130 detecting an X-ray that is radiated from the X-ray radiator 120 toward an object and transmitted through the object. The main unit 305 includes a manipulator 140 providing a user with an interface for manipulating the mobile X-ray apparatus 300, a high voltage generator 121 generating a high voltage applied to an X-ray source 122, and a controller 150 controlling overall operations of the mobile X-ray apparatus 300. The X-ray radiator 120 includes the X-ray source 122 generating the X-ray, and a collimator 123 guiding a path along which the generated X-ray is emitted from the X-ray source 122 and adjusting an irradiation region radiated by the X-ray.

The detector 130 in FIG. 3 may not be combined with any receptor, and the detector 130 may be a portable detector which can exist anywhere.

In FIG. 3, the manipulator 140 is included in the main unit 305; however, embodiments are not limited thereto. For example, as illustrated in FIG. 2, the manipulator 140 of the mobile X-ray apparatus 300 may be located on a side surface of the X-ray radiator 120.

The controller 150 controls locations of the X-ray radiator 120 and the detector 130, imaging timing, and imaging conditions according to imaging conditions set by the user.

In addition, the controller 150 generates a medical image of the object by using image data received from the detector 130. In detail, the controller 150 may generate the medical image of the object by removing noise from the image data received from the detector 130 and adjusting a dynamic range and interleaving of the image data.

The main unit 305 of the mobile X-ray apparatus 300 shown in FIG. 3 may further include an output unit (not shown) outputting the medical image generated by the controller 150. The output unit may output information that is necessary for the user to manipulate the mobile X-ray apparatus 300, for example, a UI, user information, or object information.

FIG. 4 is a schematic diagram showing a detailed configuration of a detector 400. The detector 400 may be an embodiment of the detector 130 of FIGS. 1-3. The detector 400 may be an indirect-type detector.

Referring to FIG. 4, the detector 400 may include a scintillator (not shown), a photodetecting substrate 410, a bias driver 430, a gate driver 450, and a signal processor 470.

The scintillator receives the X-ray radiated from the X-ray source 122 and converts the X-ray into light.

The photodetecting substrate 410 receives the light from the scintillator and converts the light into an electrical signal. The photodetecting substrate 410 may include gate lines GL, data lines DL, TFTs 412, photodiodes 414, and bias lines BL.

The gate lines GL may be formed in the first direction DR1, and the data lines DL may be formed in the second direction DR2 that crosses the first direction DR1. The first direction DR1 and the second direction DR2 may intersect perpendicularly to each other. FIG. 4 shows four gate lines GL and four data lines DL as an example.

The TFTs 412 may be arranged as a matrix in the first and second directions DR1 and DR2. Each of the TFTs 412 may be electrically connected to one of the gate lines GL and one of the data lines DL. A gate of the TFT 412 may be electrically connected to the gate line GL, and a source of the TFT 412 may be electrically connected to the data line DL. In FIG. 4, sixteen TFTs 412 (in a 4×4 arrangement) are shown as an example.

The photodiodes 414 may be arranged as a matrix in the first and second directions DR1 and DR2 so as to respectively correspond to the TFTs 412. Each of the photodiodes 414 may be electrically connected to one of the TFTs 412. An N-side electrode of each of the photodiodes 414 may be electrically connected to a drain of the TFT 412. FIG. 4 shows sixteen photodiodes 414 (in a 4×4 arrangement) as an example.

The bias lines BL are electrically connected to the photodiodes 414. Each of the bias lines BL may be electrically connected to P-side electrodes of an array of photodiodes 414. For example, the bias lines BL may be formed to be substantially parallel with the second direction DR2 so as to be electrically connected to the photodiodes 414. On the other hand, the bias lines BL may be formed to be substantially parallel with the first direction DR1 so as to be electrically connected to the photodiodes 414. FIG. 4 shows four bias lines BL formed along the second direction DR2 as an example.

The bias driver 430 is electrically connected to the bias lines BL so as to apply a driving voltage to the bias lines BL. The bias driver 430 may selectively apply a reverse bias voltage or a forward bias voltage to the photodiodes 414. A reference voltage may be applied to the N-side electrodes of the photodiodes 414. The reference voltage may be applied via the signal processor 470. The bias driver 430 may apply a voltage that is less than the reference voltage to the P-side electrodes of the photodiodes 414 so as to apply a reverse bias voltage to the photodiodes 414. On the other hand, the bias driver 430 may apply a voltage that is greater than the reference voltage to the P-side electrodes of the photodiodes 414 so as to apply a forward bias voltage to the photodiodes 414.

The gate driver 450 is electrically connected to the gate lines GL and thus may apply gate signals to the gate lines GL. For example, when the gate signals are applied to the gate lines GL, the TFTs 412 may be turned on by the gate signals. On the other hand, when the gate signals are not applied to the gate lines GL, the TFTs 412 may be turned off.

The signal processor 470 is electrically connected to the data lines DL. When the light received by the photodetecting substrate 410 is converted into the electrical signal, the electrical signal may be read out by the signal processor 470 via the data lines DL.

An operation of the detector 400 will now be described. During the operation of the detector 400, the bias driver 430 may apply the reverse bias voltage to the photodiodes 414.

While the TFTs 412 are turned off, each of the photodiodes 414 may receive the light from the scintillator and generate electron-hole pairs to accumulate electric charges. The amount of electric charge accumulated in each of the photodiodes 414 may correspond to the intensity of the received X-ray.

Then, the gate driver 450 may sequentially apply the gate signals to the gate lines GL along the second direction DR2. When a gate signal is applied to a gate line GL and thus TFTs 412 connected to the gate line GL are turned on, photocurrents may flow into the signal processor 470 via the data lines DL due to the electric charges accumulated in the photodiodes 414 connected to the turned-on TFTs 412.

The signal processor 470 may convert the received photocurrents into image data and output the image data to the outside. The image data may be in the form of an analog signal or a digital signal corresponding to the photocurrents.

Although not shown in FIG. 4, if the detector 400 shown in FIG. 4 is a wireless detector, the detector 400 may further include a battery unit and a wireless communication interface unit.

FIG. 5 is a block diagram of an X-ray system 2000, according to some exemplary embodiments.

Referring to FIG. 5, the X-ray system 2000 includes an X-ray apparatus 500 and a detection device 600. The X-ray apparatus 500 may include an X-ray radiator 510, a controller 520, and an output unit 530. Components in the X-ray apparatus 500 may be connected to each other via a bus 590. The descriptions above may be applied to each component of the X-ray apparatus 500, and repeated descriptions thereof will be omitted.

The detection device 600 is configured to detect X-rays radiated from the X-ray radiator 510. The detection device 600 and the X-ray apparatus 500 may be wirelessly connected or wired to each other. The detection device 600 may correspond to or include the detectors described with reference to FIGS. 1 to 4. The detection device 600 may be an independent device that may be connected to or separated from the X-ray apparatus 500. Alternatively, the detection device 600 may be a component that is included in the X-ray apparatus 500 or combined with the X-ray apparatus 500. Since an X-ray image is obtained based on X-rays detected by the detection device 600, the detection device 600 may be understood as an image receptor.

The X-ray radiator 510 of the X-ray apparatus 500 is configured to radiate X-rays.

The controller 520 may obtain arrangement information that indicates an arrangement status of the X-ray radiator 510 and the detection device 600. Also, the controller 520 may obtain quality information that indicates the quality of an X-ray image, which corresponds to the arrangement status. The controller 520 may include a central processing unit (CPU), a microprocessor, and a graphics processing unit (GPU).

The output unit 530 may output the arrangement information and the quality information that are obtained by the controller 520.

FIG. 6 is a diagram of the detection device 600 of FIG. 5, according to some exemplary embodiments.

Referring to FIG. 6, the detection device 600 may include a detector 610 and a grid 620. Since the detector 610 corresponds to the detectors described with reference to FIGS. 1 to 4, features of the detector 610 that are similar to or the same as those of the detectors of FIGS. 1 and 4 will not be repeatedly described.

The grid 620 is configured to selectively transmit X-rays that are radiated from the X-ray radiator 510 of the X-ray apparatus 500 of FIG. 5. X-rays that are radiated from the X-ray radiator 510 and transmitted through an object may include primary X-rays and scattered X-rays that are scattered due to the object. The grid 620 may be configured to transmit most of the primary X-rays but block transmission of the scattered X-rays.

The grid 620 may include a plurality of covering layers 621 that are formed of a material that blocks X-ray transmission. In the grid 620, areas between the covering layers 621 where transmission areas formed of a material that transmits X-rays. An example of the material that blocks X-ray transmission includes lead, and examples of the material that transmits X-rays include aluminum, carbon, and paper. However, examples of the materials are not limited thereto.

According to the arrangement of the covering layers 621 in the grid 620, a length 622 of a transmission area relative to a thickness 623 of the grid 620 may be adjusted. However, a form of the grid 620 is not limited thereto.

Although the detector 610 and the grid 620 are separated in FIG. 6, the separation is only an example for convenience of description. When performing X-ray imaging, the grid 620 may be used after the grid 620 is attached to the detector 610.

FIG. 7 is a diagram of an arrangement status of the X-ray radiator 510 and the detection device 600 of FIG. 5, according to some exemplary embodiments.

Referring to FIG. 7, an arrangement status of the X-ray radiator 510 and the detection device 600 may include at least one selected from parallelness of the X-ray radiator 510 and the detection device 600, a degree of matching between a center CP2 of the X-ray radiator 510 and a center CP1 of the detection device 600, and a distance (source to image-receptor distance (SID)) between the X-ray radiator 510 and the detection device 600.

The parallelness of the X-ray radiator 510 and the detection device 600 may indicate whether the X-ray radiator 510 and the detection device 600 are parallel to each other, and the parallelness may indicate non-parallelness when the X-ray radiator 510 and the detection device 600 are not parallel to each other. The parallelness of the X-ray radiator 510 and the detection device 600 may be indicated by using angles. For example, the parallelness of the X-ray radiator 510 and the detection device 600 may be indicated by using an angle AG1 formed by a normal line NL1 of the X-ray radiator 510 with the detection device 600, or complementary angles "90°-AG1" of the angle AG1. When the angle AG1 is equal to 90°, the X-ray radiator 510 and the detection device 600 are parallel to each other. When the angle AG1 is not equal to 90°, at least one of the X-ray radiator 510 and the detection device 600 has to be rotated by a complementary angle of the angle AG1, i.e., an angle of "90°-AG1", such that the X-ray radiator 510 and the detection device 600 become parallel to each other. However, the parallelness of the X-ray radiator 510 and the detection device 600 may be indicated by using methods other than the angle AG1 or the complementary angles of the angle AG1.

As another example, the parallelness may be indicated by using an incident angle of an X-ray. The incident angle of the X-ray is an angle formed by a normal line of the detection device 600 and an X-ray that is incident on the detection device 600. When the incident angle of the X-ray is close to 0°, the parallelness of the X-ray radiator 510 and the detection device 600 is substantial. That is, the X-ray radiator 510 is substantially parallel to the detection device 600.

The degree of matching between the center CP2 of the X-ray radiator 510 and the center CP1 of the detection device 600 may indicate whether the center CP2 of the X-ray radiator 510 coincides with the center CP1 of the detection device 600. When the center CP2 of the X-ray radiator 510 does not coincide with the center CP1 of the detection device 600, the degree of matching may indicate dissimilarity between the center CP2 of the X-ray radiator 510 and the center CP1 of the detection device 600.

The center CP2 of the X-ray radiator 510 may be a projected point of a center of the surface of the X-ray-radiator 510 which faces the detection device 600 onto the opposite surface of the detection device 600. For example, the degree of matching between the centers CP1 and CP2 may be indicated by using a distance between the centers CP1 and CP2 or vectors connecting the centers CP1 and CP2. When at least one of the X-ray radiator 510 and the detection device 600 is moved based on the degree of matching, the center CP2 of the X-ray radiator 510 will be the same as the center CP1 of the detection device 600.

Referring back to FIG. 5, the controller 520 may obtain at least one selected from the parallelness of the X-ray radiator 510 and the detection device 600, the degree of matching between the center CP2 of the X-ray radiator 510 and the center CP1 of the detection device 600, and the distance SID between the X-ray radiator 510 and the detection device 600. Accordingly, the controller 520 of FIG. 5 may determine the arrangement status of the X-ray radiator 510 and the detection device 600.

The controller 520 may obtain the arrangement information that indicates the arrangement status of the X-ray radiator 510 and the detection device 600. The arrangement information may include at least one selected from angle information that indicates the parallelness of the X-ray radiator 510 and the detection device 600, centering information that indicates the degree of matching between the center CP2 of the X-ray radiator 510 and the center CP1 of the detection device 600, and distance information about the distance SID between the X-ray radiator 510 and the detection device 600.

The distance information about the distance SID between the X-ray radiator 510 and the detection device 600 may include at least one selected from SID information that indicates the distance SID, and difference information that indicates a difference between the distance SID and a focal distance.

The difference between the distance SID and the focal distance may indicate whether the distance SID coincides with the focal distance. When the distance SID does not coincide with the focal distance, the difference may indicate dissimiliarity between the distance SID and the focal distance. The focal distance may be a particular distance between the X-ray radiator 510 and the detection device 600 at which a quality of an X-ray image may be optimum. The focal distance may be obtained in advance by performing preliminary experiments. Alternatively, the focal distance may be an optimum distance between the X-ray radiator 510 and the detection device 600, which is determined based on grid properties, such as an X-ray transmittance of a grid (620 of FIG. 6) of the detection device 600 and an arrangement of covering layers (621 of FIG. 6).

FIGS. 8 and 9 are exemplary graphs showing a quality of an X-ray image according to parallelness of an X-ray radiator and a detection device.

Referring to FIGS. 8 and 9, an x-axis in each of the graphs represents angles that indicate the parallelness of the X-ray radiator and the detection device. The angles may be the complementary angles "90°-AG1" of the angle AG1 described with reference to FIG. 7. Alternatively, the x-axes may represent incident angles of an X-ray. When the incident angle of an X-ray is 0°, the X-ray radiator and the detection device are parallel to each other. In the graphs, ratios 8:1, 6:1, 4:1, and 3:1 are examples of a ratio between the thickness 623 of the grid 620 and the length 622 of the transmission area of FIG. 6.

In FIG. 8, a y-axis of the graph represents a contrast improvement factor of an X-ray image. The quality of the X-ray image improves as the contrast improvement factor of an X-ray image increases. Referring to the graph of FIG. 8, as an angle approaches 0°, i.e., as the parallelness of the X-ray radiator and the detection device increases, the contrast improvement factor of an X-ray image increases. Accordingly, when the parallelness of the X-ray radiator and the detection device is substantial, the quality of the X-ray image improves. Also, as the ratio between the thickness 623 of the grid 620 and the length 622 of the transmission area of FIG. 6 increases, the contrast improvement factor with respect to angles increases in the order of 3:1, 4:1, 6:1, and 8:1 in the graph.

In FIG. 9, a y-axis of the graph represents optical density. The optical density is a ratio between the amount of X-rays incident on a grid (620 of FIG. 6) and the amount of X-rays that transmitted through the grid (620 of FIG. 6) and reached a detector (610 of FIG. 6). As the optical density increases, the quality of the X-ray image improves. Referring to the graph of FIG. 9, as an angle approaches 0°, i.e., as the parallelness of the X-ray radiator and the detection device increases, the optical density also increases. Therefore, as the parallelness of the X-ray radiator and the detection device increases, the quality of the X-ray image improves. Also, as the ratio between the thickness 623 of the grid 620 and the length 622 of the transmission area of FIG. 6 increases, the attenuation of the optical density with respect to angles increases in the order of 3:1, 4:1, 6:1, and 8:1 in the graph.

Accordingly, in FIG. 5, the arrangement status of the X-ray radiator 510 and the detection device 600 affects the quality of the X-ray image that is to be obtained via the detection device 600. The better the arrangement status of the X-ray radiator 510 and the detection device 600 is, the higher the quality of the X-ray image will be. For example, as the parallelness of X-ray radiator 510 and the detection device 600 increases, as the degree of matching between the center of the X-ray radiator 510 and the center of the detection device 600 increases, or as the difference between the distance between the X-ray radiator 510 and the detection device 600 and the focal distance decreases, the quality of the X-ray image improves. In particular, when the X-ray radiator 510 and the detection device 600 are parallel to each other, the center of the X-ray radiator 510 is the same as the center of the detection device 600, and the distance between the X-ray radiator 510 and the detection device 600 is the same as the focal distance, the arrangement status of the X-ray radiator 510 and the detection device 600 is exactly accurate.

The controller 520 may obtain the arrangement information that indicates the arrangement status of the X-ray radiator 510 and the detection device 600, and the quality information that indicates the quality of the X-ray image that is to be obtained with respect to the arrangement status.

FIG. 10 is a diagram of the output unit 530 of FIG. 5, according to some exemplary embodiments.

Referring to FIGS. 5 and 10, the output unit 530 may output arrangement information 531 and quality information 532.

The arrangement information 531 indicates the arrangement status of the X-ray radiator 510 and the detection device 600. The output unit 530 may output the arrangement information 531 by using at least one of characters, numbers, figures, colors, and a combination thereof such that a user may recognize the arrangement status of the X-ray radiator 510 and the detection device 600 based on the arrangement information 531.

The quality information 532 indicates the quality of the X-ray image, which corresponds to the arrangement status. The output unit 530 may output the quality information 532 by using at least one of characters, numbers, figures, colors, and a combination thereof such that the user may recognize the quality of the X-ray image, which corresponds to the arrangement status, based on the quality information 532.

As described above, according to some exemplary embodiments, the user may recognize the arrangement status of the X-ray radiator 510 and the detection device 600 based on the arrangement information 531, and whether the quality of the X-ray image corresponding to the arrangement status is appropriate. When the quality of the X-ray image is appropriate, the X-ray system 2000 may obtain the X-ray image while maintaining the arrangement status. When the quality of the X-ray image is not appropriate, the X-ray system 2000 may change the arrangement status by adjusting a location of at least one the X-ray radiator 510 and the detection device 600, and then obtain the X-ray image.

In particular, the above-described exemplary embodiments will be very useful when the user cannot identify the arrangement status of the X-ray radiator 510 and the detection device 600 in person, for example, when the detection device 600 is located on an object and the detection device 600 is covered by the object. Also, the exemplary embodiment will be very useful when the user cannot identify the arrangement status of the X-ray radiator 510 and the detection device 600, for example, when the detection device 600 is a portable type that is not coupled to a receptor (e.g., 280 and 290 of FIG. 2) and may be provided at a random location.

According to some exemplary embodiments, based on the arrangement information 531 and the quality information 532 that are output from the output unit 530, the user may recognize not only the arrangement status, but also the quality of the X-ray image corresponding to the arrangement status. Accordingly, the X-ray apparatus 500 may provide greatly improved user convenience.

Other than the arrangement information 531 and the quality information 532, the output unit 530 of FIG. 5 may further output relationship information that indicates qualities of X-ray images, which respectively correspond to a plurality of arrangement ranges that may be formed between the X-ray radiator 510 and the detection device 600. This will be described below with reference to the following drawings.

FIG. 11 is a diagram of an output unit 700, according to some exemplary embodiments. Since the output unit 700 of FIG. 11 corresponds to the output unit 530 of FIG. 5, features of the output unit 700 that are similar to or the same as those of the output unit 530 will not be repeatedly described.

Referring to FIG. 11, the output unit 700 may output relationship information ("SID," "centering," and "angle") that indicates qualities "Good," "Normal," and "Poor" of X-ray images, which respectively correspond to a plurality of arrangement ranges [(D0~D1, D1~D2, and D2~D3), (C0~C1, C1~C2, and C2~C3), and (A0~A1, A1~A2, and A2~A3)] that may be formed between the X-ray radiator and the detection device. The output unit 700 may output the relationship information ("SID," "centering," and "angle") such that the qualities "Good," "Normal," and "Poor" of the X-ray images are distinguished from each other by using different colors CL1, CL2, and CL3. For example, a color CL1 that represents "Good" quality may be green, a color CL2 that represents "Normal" quality may be yellow, and a color CL3 that represents "Poor" quality may be red. However, the colors are not limited thereto.

"Good" quality may indicate a state in which the arrangement status of the X-ray radiator and the detection device is exactly accurate, or a state in which the arrangement status of the X-ray radiator and the detection device is not exactly accurate but the quality of an X-ray image has an insignificant difference with that in the state in which the arrangement status is exactly accurate.

"Normal" quality may indicate a state in which the arrangement status of the X-ray radiator and the detection device is not exactly accurate, and thus the quality of an X-ray image is slightly low but adequate enough for a user to diagnose an object by using the X-ray image.

"Poor" quality may indicate a state in which the accuracy of the arrangement status of the X-ray radiator and the detection device is too low and thus a quality of an X-ray image is inappropriate for diagnosing an object.

The output unit 700 may output a table 74 that indicates the qualities "Good," "Normal," and "Poor" of the X-ray image and the colors CL1, CL2, and CL3 that represent each quality. Although the quality of the X-ray image is classified into 3 types in FIG. 11, types of the quality are not limited thereto.

In the relationship information, "SID" may indicate the qualities "Good," "Normal," and "Poor" of the X-ray image respectively corresponding to the plurality of arrangement ranges "D0~D1, D1~D2, and D2~D3" related to a distance and may be formed between the X-ray radiator and the detection device. Specifically, "SID" of the relationship information may indicate "Good" quality of the X-ray image corresponding to the arrangement range "D0~D1" by using the color CL1, "Normal" quality of the X-ray image corresponding to the arrangement range "D1~D2" by using the color CL2, and "Poor" quality of the X-ray image corresponding to the arrangement range "D2~D3" by using the color CL3.

In the relationship information, "centering" may indicate the quality "Good," "Normal," and "Poor" of the X-ray image respectively corresponding to the plurality of arrangement ranges "C0~C1," "C1~C2," and "C2~C3" that are related to a degree of matching and may be formed between a center of the X-ray radiator and a center of the detection device. Specifically, "centering" of the relationship information may indicate "Good" quality of the X-ray image corresponding to the arrangement range "C0~C1" by using the color CL1, "Normal" quality of the X-ray image corresponding to the arrangement range "C1~C2" by using the color CL2, and "Poor" quality of the X-ray image corresponding to the arrangement range "C2~C3" by using the color CL3.

In relationship information, "angle" may indicate the qualities "Good," "Normal," and "Poor" of the X-ray image which respectively correspond to the plurality of arrangement ranges "A0~A1," "A1~A2," and "A2~A3" that are related to parallelness and may be formed between the X-ray radiator and the detection device. Specifically, "angle" of the relationship information may indicate "Good" quality of the X-ray image corresponding to the arrangement range "A0~A1" by using the color CL1, "Normal" quality of the X-ray image corresponding to the arrangement range "A1~A2" by using the color CL2, and "Poor" quality of the X-ray image corresponding to the arrangement range "A2~A3" by using the color CL3.

Accordingly, based on the relationship information ("SID," "centering," and "angle") that is output from the output unit 700, the user may intuitively recognize the qualities "Good," "Normal," and "Poor" of the X-ray image, which respectively correspond to the plurality of arrangement ranges [(D0~D1, D1~D2, D2~D3), (C0~C1, C1~C2, C2~C3), and (A0~A1, A1~A2, A2~A3)].

Also, the output unit 700 may output pieces of arrangement information 71, 72, and 73 that indicate the arrangement status of the X-ray radiator and the detection device. On relationship information ("SID," "centering," and "angle"), the pieces of arrangement information 71, 72, and 73 may respectively indicate in which arrangement range (D0~D1, C1~C2, and A2~A3) from among the plurality of arrangement ranges [(D0~D1, D1~D2, D2~D3), (C0~C1, C1~C2, C2~C3), and (A0~A1, A1~A2, A2~A3)] the arrangement status is included.

The arrangement information 71 is output to "SID" of the relationship information and indicates that the distance between the X-ray radiator and the detection device is included in the arrangement range "D0~D1." When the arrangement information 71 is output to the "SID" of the relationship information, the quality "Good" that corresponds to the arrangement information 71 is shown by using the color CL1.

The arrangement information 72 is output to "centering" of the relationship information and indicates that the degree of matching between the center of the X-ray radiator and the center of the detection device is within the arrangement range "C1~C2." When the arrangement information 72 is output to the "centering" of the relationship information, the quality "Normal" that corresponds to the arrangement information 72 is shown by using the color CL2.

The arrangement information 73 is output to "angle" of the relationship information and indicates that the parallelness of the X-ray radiator and the detection device is within the arrangement range "A2~A3." The quality "Poor" that corresponds to the arrangement information 73 is shown by using the color CL3.

Accordingly, when the pieces of arrangement information 71, 72, and 73 are respectively shown on the pieces of relationship information "SID," "centering," and "angle," the output unit 700 may also show quality information that corresponds to the arrangement status via the pieces of relationship information "SID," "centering," and "angle."

Also, the output unit 700 may further output quality information 75 that indicates an overall quality ("Normal" in FIG. 11) that corresponds to the arrangement status that includes the distance between the X-ray radiator and the detection device, the degree of matching between the center of the X-ray radiator and the center of the detection device, and the parallelness of the X-ray radiator and the detection device. Although the quality information 75 is distinguished from other qualities "Good" and "Poor" on the table 74 in FIG. 11, exemplary embodiments are not limited thereto.

The relationship information ("SID," "centering," and "angle") and the pieces of arrangement information 71, 72, and 73 that are output from the output unit 700 in FIG. 11 are only examples. The output unit 700 may output the relationship information, the arrangement information, and the quality information by using at least one of characters, numbers, figures, colors, and a combination thereof such that the user may intuitively recognize each piece of information.

FIG. 12 is a block diagram of an X-ray system 3000, according to some exemplary embodiments.

Referring to FIG. 12, the X-ray system 3000 includes an X-ray apparatus 800 and a detection device 900. The X-ray apparatus 800 may include an X-ray radiator 810, a controller 820, an output unit 830, an input unit 840, and a memory 850. Components in the X-ray apparatus 800 may be connected to each other via a bus 890. The descriptions above may be applied to each component of the X-ray apparatus 800, and repeated descriptions thereof will be omitted.

The input unit 840 may receive, from a user, commands for setting or re-setting relationship information that indicates qualities of an X-ray image that respectively correspond to a plurality of arrangement ranges that may be formed between the X-ray radiator 810 and the detection device 900. In this case, the output unit 830 may output a UI by which the user may identify the relationship information and set or re-set the relationship information.

The input unit 840 may receive, from the user, an adjustment command for adjusting a location of at least one of the X-ray radiator 810 and the detection device 900. The input unit 840 may receive, from the user, a radiation command for instructing the X-ray radiator 810 to radiate X-rays.

Based on the arrangement information and the quality information output from the output unit 830, the user may determine whether quality of the X-ray image, which corresponds to the arrangement status of the X-ray radiator 810 and the detection device 900, is appropriate.

When the user determines that the quality of the X-ray image is not appropriate based on the quality information, the user may input the adjustment command into the input unit 840. When the user determines that the quality of the X-ray image is appropriate based on the quality information, the user may input the radiation command to the input unit 840.

The controller 820 may control an operation of at least one of the X-ray radiator 810 and the detection device 900 based on the adjustment command or the radiation command. Based on the adjustment command, the controller 820 may change the arrangement status by adjusting the location of at least one of the X-ray radiator 810 and the detection device 900. Based on the radiation command, the controller 820 may control the X-ray radiator 810 to radiate X-rays.

After the input unit 840 has received the adjustment command, when the arrangement status of the X-ray radiator 810 and the detection device 900 is changed under the control of the controller 820, the output unit 830 may re-output arrangement information that indicates the changed arrangement status and quality information that indicates the quality of the X-ray image which corresponds to the changed arrangement status. That is, the output unit 830 may output the arrangement status of the X-ray radiator 810 and the detection device 900 in real-time.

Based on the arrangement information and the quality information that are output again by the output unit 830, the user may re-determine whether the quality of the X-ray image, which corresponds to the arrangement status of the X-ray radiator 810 and the detection device 900, is appropriate, and according to the determination result, the user may re-input the adjustment command or the radiation command to the input unit 840.

The memory 850 may store the relationship information. Also, when the relationship information is set or rest, the memory 850 may update the relationship information and store the updated relationship information. The relationship information may vary depending on an object to be captured by X-ray imaging. For example, an X-ray image may be less affected by the arrangement status when the object is a hand or a foot, compared to when the object is a chest area. Therefore, the relationship information stored in the memory 850 when the object is the chest area may be different from the relationship information stored in the memory 850 when the object is the hand or the foot.

Depending on a type of the object, the user may set or re-set the relationship information via the input unit 840. Alternatively, when the user inputs a type of the object to the input unit 840, the controller 820 may search the relationship information in the memory 850 based on the type of the object and obtain a quality that corresponds to the arrangement status.

FIG. 13 is a diagram of a UI that is output by the output unit 830 of FIG. 12, according to some exemplary embodiments.

Referring to FIGS. 12 and 13, the output unit 830 may output a UI 89 by which the user may identify the pieces of relationship information "SID," "centering," and "angle," and set or re-set the pieces of relationship information "SID," "centering," and "angle."

On the UI 89, the pieces of relationship information "SID," "centering," and "angle" show qualities of an X-ray image, which respectively correspond to a plurality of arrangement ranges that may be formed between the X-ray radiator 810 and the detection device 900. In the pieces of relationship information "SID," "centering," and "angle," the qualities of the X-ray image may be distinguished from each other by using different colors (CL1, CL2, . . . , CLN).

A user 20 may input a command for setting or re-setting the relationship information ("SID," "centering," and "angle") to the input unit 840. The command for setting or re-setting the relationship information ("SID," "centering," and "angle") may include at least one selected from a command for setting or re-setting the plurality of arrangement ranges, a command for setting or re-setting the qualities of the X-ray image, which respectively correspond to the plurality of arrangement ranges, and a command for setting or re-setting colors for distinguishing the qualities of the X-ray image, which respectively correspond to the plurality of arrangement ranges, from each other.

For example, the user 20 may input, into the input unit 840, a command for setting or re-setting a plurality of arrangement ranges "1~2 cm," "2~4 cm" . . . "10~25 cm," in "centering" of the relationship information. As another example, the user 20 may input a command for setting or re-setting a quality of an X-ray image which corresponds to an arrangement range of 30~40° from "Poor" to "Very Poor" in "angle" of the relationship information. As another example, the user 20 may input a command for setting or re-setting a color that represents "Good" quality from green to blue. However, a command for setting or re-setting is not limited to the examples above.

When the input unit 840 includes a touch screen, the touch screen may be provided on the output unit 830. The user 20 may input a command for setting or re-setting by touch. However, the method of inputting a command shown in FIG. 13 is only an example, and the method of inputting a command may vary according to embodiments of the input unit 840.

FIG. 14 is a diagram of the output unit 830 of FIG. 12, according to some exemplary embodiments.

Referring to FIG. 14, the output unit 830 may output relationship information ("SID," "centering," and "angle") that show qualities "Very good," "Good," "Normal," "Poor," and "Very poor" of an X-ray image, which respectively correspond to a plurality of arrangement ranges [(D0~D1, D1~D2, D2~D3, D3~D4, D4~D5), (C0~C1, C1~C2, C2~C3, C3~C4, C4~C5), (A0~A1, A1~A2, A2~A3, A3~A4, A4~A5)] that may be formed between an X-ray radiator and a detection device. On the relationship information ("SID," "centering," and "angle") the output unit 700 may output the qualities "Very good," "Good," "Normal," "Poor," and "Very poor" of the X-ray image by using different colors CL1, CL2, CL3, CL4, and CL5 so that the qualities may be distinguished from each other.

In comparison to FIG. 11, the qualities of the X-ray image are classified into 3 types ("Good," "Normal," and "Poor") in FIG. 11, whereas the qualities of the X-ray image are classified into 5 types ("Very good," "Good," "Normal," "Poor," and "Very poor") in FIG. 14. For example, by using the output unit 830 and the input unit 840 of FIGS. 12 and 13, a user may re-set the relationship information of FIG. 11 as the relationship information as shown in FIG. 14. In this case, the user may change the relationship information by inputting, to the input unit 840, a command for re-setting 3 arrangement ranges into 5 arrangement ranges, a command for re-setting qualities of an X-ray image, which respectively correspond to the 5 arrangement ranges, and a command for re-setting colors that distinguish the qualities of the X-ray image from each other from 3 colors to 5 colors.

Referring to FIG. 14, the output unit 700 may output pieces of arrangement information 81, 82, and 83 that indicate the arrangement status of the X-ray radiator and the detection device. The output unit 830 may further output a table 84 that indicates the qualities "Very good," "Good," "Normal," "Poor," and "Very poor" of the X-ray image and the colors CL1, CL2, CL3, CL4, and CL5 that represent each quality.

Also, the output unit 830 may further output quality information 86 that indicates an overall quality ("Good" in FIG. 14) that corresponds to the arrangement status that includes a distance between the X-ray radiator and the detection device, a degree of matching between a center of the X-ray radiator and a center of the detection device, and parallelness of the X-ray radiator and the detection device. Although the quality information 86 is distinguished from other qualities "Very good," "Normal," "Poor," and "Very poor" on the table 84 in FIG. 14, exemplary embodiments are not limited thereto.

FIG. 15 is a diagram of relationship information stored in the memory 850 of FIG. 12, according to some exemplary embodiments.

Referring to FIGS. 12 and 15, the relationship information in the memory 850 may include a plurality of tables TB1 to TBN. Each of the plurality of tables TB1 to TBN corresponds to an arrangement range from among the plurality of arrangement ranges that are related to a degree of matching and may be formed between a center of the X-ray radiator 810 and a center of the detection device 900.

An example as shown in FIG. 14, in which the plurality of arrangement ranges relative to the degree of matching are "C0~C1, C1~C2, C2~C3, C3~C4, and C4~C5," will be described. From among the plurality of tables TB1 to TBN, a first table TB1 corresponds to "first centering" in which an arrangement range is [C0~C1], a second table TB2 corresponds to "second centering" in which an arrangement range is [C1~C2], a third table TB3 corresponds to "third centering" in which an arrangement range is [C2~C3], a fourth table TB4 corresponds to "fourth centering" in which an arrangement range is [C3~C4], and a fifth table TB5 corresponds to "fifth centering" in which an arrangement range is [C4~C5].

According to a corresponding degree of matching, each of the plurality of tables TB1 to TBN stores qualities "Good," "Normal," and "Poor" of an X-ray image according to parallelness ("angle") that may be formed between the X-ray radiator 810 and the detection device 900 and a distance ("SID") that may be formed between the X-ray radiator 810 and the detection device 900.

As shown in FIG. 15, the memory 850 may store the plurality of tables TB1 to TBN such that the qualities "Good," "Normal," and "Poor" of the X-ray image are distinguished from each other by using different colors CL1, CL2, and CL3. The memory 850 may additionally store a table LT that shows a relationship between the colors CL1, CL2, and CL3 that respectively represent the qualities "Good," "Normal," and "Poor" of the X-ray image. Although there are 3 types of qualities of the X-ray image in FIG. 15, the qualities are not limited thereto.

A plurality of arrangement ranges relative to the parallelness ("angle") may be [<−10°, −10°~−5°, −5°~0°, 0°, 0°~5°, 5°~10°, and >+10°]. However, FIG. 15 is only an example, and exemplary embodiments are not limited to FIG. 15.

A plurality of arrangement ranges relative to the distance ("SID") may be [>f2, f2/2~f2, f0~f2/2, f0, f1/2~f0, f1~f1/2, and >f1]. Here, 'f0' represents a focal distance, i.e., a distance between an X-ray radiator and a detection device, at which the qualities of the X-ray image may be optimum, 'f1' represents a lower limit range of the focal distance (f0), and 'f2' represents an upper limit range of the focal distance (f0). The plurality of arrangement ranges relative to the distance ("SID") shown in FIG. 15 may indicate a difference between the focal distance (f0) and the distance between the X-ray radiator and the detection device. However, FIG. 15 is only an example, and exemplary embodiments are not limited to FIG. 15.

The controller 820 may determine in which arrangement range a degree of matching between the center of the X-ray radiator 810 and the center of the detection device 900 is included, in which arrangement range parallelness of the X-ray radiator 810 and the detection device 900 is included, and in which arrangement range a distance between the X-ray radiator 810 and the detection device 900 is included, and thus, determine the arrangement status of the X-ray radiator 810 and the detection device 900. Then, the controller 820 may determine a quality of the X-ray image which corresponds to an arrangement status that is determined based on the tables TB1 to TBN and LT stored in the memory 850.

For example, the controller 820 may determine that the degree of matching is included in the arrangement range "first centering," the parallelness is included in the arrangement range "−10°~−5°," and the distance is included in the arrangement range "f0~f2/2," and then determine the arrangement status of the X-ray radiator 810 and the detection device 900. Based on the tables TB1 to TBN and LT stored in the memory 850, the controller 820 may determine that the quality of the X-ray image is "Normal," which is distinguished from other qualities by using the color CL2.

As shown in FIG. 15, default values of the relationship information stored in the memory 850 may be obtained in advance by performing preliminary experiments with a phantom. Next, when the relationship information is set or re-set by the user, the memory 850 may update the relationship information and store the updated relationship information.

FIG. 16 is a diagram of the output unit 830 of FIG. 12, according to some exemplary embodiments.

Referring to FIGS. 12 and 16, it is assumed that the controller 820 determines that the degree of matching is included in an arrangement range "n-th centering," the parallelness is included in an arrangement range "0°~+5°," and the distance is included in an arrangement range "f1~f1/2," and then determines the arrangement status of the X-ray radiator 810 and the detection device 900. The output unit 830 may output an n-th table TBn that corresponds to the "n-th centering," from among the tables TB1 to TBN stored in the memory 850. The output unit 830 may output arrangement information 85 on the n-th table TBn to show the arrangement information 85 that indicates the arrangement status of the X-ray radiator 810 and the detection device 900 is. The arrangement information 85 may be output by using a method by which the user may easily recognize the arrangement information 85 on the n-th table TBn.

Also, when the arrangement information 85 is shown on the n-th table TBn, the quality "Normal" of the X-ray image, which corresponds to the arrangement status, is shown by using the color CL2.

The output unit 830 may output the arrangement information 85 and quality information (CL2: Normal) on the n-th table TBn by using at least one of characters, numbers, figures, colors, and a combination thereof so that the user may recognize the arrangement status and the quality that corresponds to the arrangement status.

FIG. 17 is a diagram of the output unit 830 of FIG. 12, according to some exemplary embodiments.

Referring to FIGS. 12 and 17, the output unit 830 may output pieces of arrangement information 91, 92, and 93 that indicates the arrangement status of the X-ray radiator 810 and the detection device 900.

The pieces of arrangement information 91, 92, and 93 may include a first icon 91 that is visually associated with the detection device 900, and a second icon 92 that is visually associated with the center of the X-ray radiator 810. The output unit 830 may output the first icon 91 and the second icon 92 based on the arrangement status of the X-ray radiator 810 and the detection device 900. That is, based the degree of matching between the center of the X-ray radiator 810 and the center of the detection device 900 and the distance between the X-ray radiator 810 and the detection device 900, the first icon 91 and the second icon 92 may be 3-dimensionally arranged on a screen of the output unit 830.

The output unit 830 may further output a normal line 99 of the first icon 91 which corresponds to a normal line of the detection device 900. Accordingly, based on a degree of matching between the second icon 92 and the normal line 99, the user may intuitively recognize the degree of matching between the center of the X-ray radiator 810 and the center of the detection device 900.

Also, by using different colors CL1, CL2, and CL3, the output unit 830 may output qualities "Good," "Normal," and "Poor" of an X-ray image, which respectively correspond to a plurality of arrangement ranges R1, R2, and R3 that may be formed between the X-ray radiator 810 and the detection device 900, so that the qualities may be distinguished from each other. By doing so, relationship information (R1: Good, R2: Normal, and R3: Poor) is output. That is, with regard to the relationship information (R1: Good, R2: Normal, and R3: Poor) in FIG. 17, cones that respectively represent the plurality arrangement ranges R1, R2, and R3 are shown by using the colors CL1, CL2, and CL3 that respectively correspond to the qualities, and thus, the qualities "Good," "Normal," and "Poor" of the X-ray image, which respectively correspond to the plurality of arrangement ranges R1, R2, and R3, may be indicated.

The output unit 830 may output a table LT that shows a relationship between the qualities "Good," "Normal," and "Poor" of the X-ray image and the colors CL1, CL2, and CL3 that represent each quality.

On the relationship information (R1: Good, R2: Normal, and R3: Poor), the output unit 830 may output the second icon 92 that is visually associated with the center of the X-ray radiator 810. That is, based on the second icon 92, it may be recognized that the arrangement status of the X-ray radiator 810 and the detection device 900 is included in a second arrangement range R2 from among the plurality of arrangement ranges R1, R2, and R3. Also, based on the relationship information (R1: Good, R2: Normal, and R3: Poor), the quality "Normal" of the X-ray image, which corresponds to the arrangement status, is shown by using the color CL2.

Also, the pieces of arrangement information 91, 92, and 93 that are output from the output unit 830 may further include angle information 93 that indicates the parallelness of the X-ray radiator 810 and the detection device 900. The angle information 93 may be output as characters, numbers, or figures, for example, "angle: −7°," as shown in FIG. 17. Also, the angle information 93 may further include the color CL2 and output. Accordingly, via the color CL2, the angle information 93 may additionally indicate quality information that indicates that a quality that corresponds to the parallelness ("angle: −7°") is "Normal."

Since the user may intuitively recognize the arrangement status and the quality that corresponds to the arrangement status via the arrangement information 91, 92, and 93, the user may easily recognize how to manipulate the X-ray system 3000.

According to the example of FIG. 17, since the quality that corresponds to the arrangement status is "Normal," when the user determines that the "Normal" quality is appropriate, the user may input, into the input unit 840, a radiation command for instructing the X-ray radiator 810 to radiate X-rays. For example, when an object is in pain, when X-ray imaging has to be quickly finished because an object is an emergency patient, or when a high-quality X-ray image is not required, the user may input the radiation command to quickly finish X-ray imaging.

When the user determines that the "Normal" quality is not appropriate, the user may input, into the input unit 840, an adjustment command for adjusting a location of at least one of the X-ray radiator 810 and the detection device 900. Based on the pieces of arrangement information 91, 92, and 93 and the relationship information (R1: Good, R2: Normal, and R3: Poor) that are output from the output unit 830, the user may intuitively and easily recognize how to adjust the location of at least one of the X-ray radiator 810 and the detection device 900 so as to obtain an X-ray image with "Good" quality.

For example, according to the example shown in FIG. 17, based on the second icon 92 that is visually associated with the center of the X-ray radiator 810 and shown on the relationship information (R1: Good, R2: Normal, and R3: Poor), the user may easily recognize that the arrangement range R2, i.e., "Normal" quality, is not changed to the arrangement range R1, i.e., "Good" quality, by adjusting only the degree of matching between the center of the X-ray radiator 810 and the center of the detection device 900 or only the distance between the X-ray radiator 810 and the detection device 900.

Therefore, the user may input, into the input unit 840, the adjustment command that adjusts at least one of the X-ray radiator 810 and the detection device 900 so as to adjust both the degree of matching and the distance. When the location of the at least one of the X-ray radiator 810 and the detection device 900 is changed according to the adjustment command, the arrangement status of the X-ray radiator 810 and the detection device 900 may be changed. The output unit 830 may output again the pieces of arrangement information 91, 92, and 93 that represent the changed arrangement status. For example, after the adjustment command is input, a location of the second icon 92 on the relationship information (R1: Good, R2: Normal, and R3: Poor) may be changed.

As another example, the user may first input the adjustment command into the input unit 840 so that the parallelness is adjusted. When the parallelness is adjusted by doing so, the output unit 830 may also output an adjusted result. The angle information 93 may be output again to represent the adjusted parallelness. Also, when the parallelness is adjusted, the relationship information (R1: Good, R2: Normal, and R3: Poor) may be changed, and the output unit 830 may output the changed result. When the parallelness is adjusted, the plurality of arrangement ranges R1, R2, and R3 may be changed, and cones that are accordingly changed may be output again. Also, due to the change in the relationship information (R1: Good, R2: Normal, and R3: Poor), the arrangement range that includes the second icon 92 may be changed from "R2" to another arrangement range. The user may recognize the arrangement information 91, 92, and 93 and the relationship information (R1: Good, R2: Normal, and R3: Poor) that are output again from the output unit 830, and then adjust the degree of matching between the centers or the distance.

FIG. 18 is a block diagram of an X-ray system 4000, according to some exemplary embodiments.

Referring to FIG. 18, the X-ray system 4000 includes an X-ray apparatus 5000 and a detection device 6000. The X-ray apparatus 5000 may include an X-ray radiator 5100, a controller 5200, an output unit 5300, an input unit 5400, a memory 5500, and a location information acquirer 5600. Components in the X-ray apparatus 5000 may be connected to each other via a bus 5900. The descriptions above may be applied to each component of the X-ray apparatus 5000, and repeated descriptions thereof will be omitted.

The location information acquirer 5600 is configured to obtain location information of at least one of the X-ray radiator 5100 and the detection device 6000. For example, the location information acquirer 5600 may obtain a distance between the X-ray radiator 5100 and the detection device 6000, a location in a 3D space such as (x, y, z) coordinates of at least one of the X-ray radiator 5100 and the detection device 6000, or rotation information or orientation information of at least one of the X-ray radiator 5100 and the detection device 6000. The rotation information of at least one of the X-ray radiator 5100 and the detection device 6000 may include a rotation angle relative to a vertical plane or a horizontal plane.

For example, the location information acquirer 5600 may include, but is not limited to, an image capturing device, a laser source, a gyroscope, an inertial measurement unit (IMU), an accelerometer, a magnetometer, and a GPS sensor. The location information acquirer 5600 may obtain the location information of at least one of the X-ray radiator 5100 and the detection device 6000 by using various methods, such as light, radio waves, sound waves, a magnetic field, and an electric field.

The detection device 6000 may also include a location information acquirer 6300. The location information acquirer 6300 of the detection device 6000 may also be configured to obtain location information of at least one of the X-ray radiator 5100 and the detection device 6000. The detection device 6000 may transmit the location information obtained by the location information acquirer 6300 to the X-ray apparatus 5000. The detection device 6000 may transmit the location information via wire or wirelessly. Accordingly, each of the X-ray apparatus 5000 and the detection device 6000 may further include a communicator (not shown). The location information acquirer 6300 may be included in a detector or a grid included in the detection device 6000.

Although each of the X-ray apparatus 5000 and the detection device 6000 includes a location information acquirer (5600 and 6300) in FIG. 18, only one of the X-ray apparatus 5000 and the detection device 6000 may be including a location information acquirer.

Based on the location information obtained by the location information acquirers 5600 and 6300, the controller 5200 may determine arrangement status of the X-ray radiator 5100 and the detection device 6000.

The output unit 5300 may output arrangement information that indicates the arrangement status and quality information that corresponds to the arrangement status.

FIG. 19 is a block diagram of an X-ray system 7000, according to some exemplary embodiments.

Referring to FIG. 19, the X-ray system 7000 may include a workstation 7300, an X-ray apparatus 7500, and a detection device 7600. The X-ray apparatus 7500 includes an X-ray radiator 7510.

The workstation 7300 may include a controller 7320 and an output unit 7330. The workstation 7300 may be wired or wirelessly connected to the X-ray apparatus 7500. Also, the workstation 7300 may be wired or wirelessly connected to the detection device 7600.

The features of the controllers and the output units of the X-ray apparatuses described above may be applied to the controller 7320 and the output unit 7330 of the workstation 7300. Also, a UI that is output from the output unit 7330 of the workstation 7300 may corresponds to a UI that is output from an output unit of an X-ray apparatus. Accordingly, a simple and intuitive UI may be provided, and thus, a user may conveniently manipulate or control the X-ray apparatus 7500 by intuition.

The controller 7320 may obtain arrangement information that indicates the arrangement status of the X-ray radiator 7510 and the detection device 7600. To do so, the controller 7320 may receive location information of at least one of the X-ray radiator 7510 and the detection device 7600 from the X-ray apparatus 7500. The controller 7320 may receive the location information of at least one of the X-ray radiator 7510 and the detection device 7600 from the detection device 7600.

The controller 7320 may obtain quality information that indicates the quality of an X-ray image that corresponds to the arrangement status. The output unit 7330 may output the arrangement information and the quality information that are obtained by the controller 7320. Also, the output unit 7330 may further output relationship information that indicates qualities of an X-ray image, which respectively correspond to a plurality of arrangement ranges that may be formed between the X-ray radiator 7510 and the detection device 7600. The features of the output units of the X-ray apparatuses described above may also be applied to the arrangement information, the quality information, and the relationship information that are output from the output unit 7330.

FIG. 20 is a block diagram of a workstation 8300, according to some exemplary embodiments. The workstation 8300 of FIG. 20 may be an exemplary embodiment of the workstation 7300 of FIG. 19.

Referring to FIGS. 19 and 20, the workstation 8300 may include a controller 8320, an output unit 8330, an input unit 8340, and a memory 8350. The features of the input units and the memories of the X-ray apparatuses described above may be applied to the input unit 8340 and the memory 8350 of the workstation 8300.

The input unit 8340 may receive a command for setting or re-setting relationship information from a user. Also, from the user, the input unit 8340 may receive at least one of an adjustment command for adjusting a location of at least one of the X-ray radiator 7510 and the detection device 7600 and a radiation command for instructing the X-ray radiator 7510 to radiate X-rays.

The controller 8320 may set or re-set the relationship information based on a command of the user. Also, the controller 8320 may control operations of at least one of an X-ray radiator and a detection device of an X-ray apparatus.

FIG. 21 is a flowchart of a method S100 of operating an X-ray system, according to some exemplary embodiments.

Referring to FIG. 21, the X-ray system may obtain arrangement information that indicates the arrangement status of an X-ray radiator and a detection device of an X-ray apparatus (S110). The X-ray system may obtain quality information that indicates the quality of an X-ray image, which corresponds to the arrangement status (S120).

The X-ray system may output the arrangement information and the quality information (S130). In this case, the arrangement information and the quality information may be output with relationship information that indicates qualities of an X-ray image, which respectively correspond to a plurality of arrangement ranges that may be formed between the X-ray radiator and the detection device.

The X-ray system may receive, from a user, at least one of an adjustment command for adjusting a location of at least one of the X-ray radiator and the detection device, and a radiation command for instructing the X-ray radiator to radiate X-rays. Based on the adjustment command or the radiation command, the X-ray system may control operations of at least one of the X-ray radiator and the detection device.

The method S100 of operating the X-ray system of FIG. 21 may be performed in the X-ray systems, X-ray apparatuses, and workstations shown in the drawings above. The method S100 of operating the X-ray system may be performed as described above.

According to some exemplary embodiments, a user may easily recognize arrangement status of an X-ray radiator and a detection device based on arrangement information, and whether a quality of an X-ray image, which corresponds to the arrangement status, is appropriate. Accordingly, the user may easily determine how to manipulate an X-ray system, for example, whether to re-adjust the arrangement status of the X-ray radiator and the detection device, or whether to proceed with X-ray imaging without re-adjusting the arrangement status. For Also, when the arrangement information and quality information are output with relationship information, based on the arrangement information and the quality information, the user may easily recognize how much the arrangement status has to be adjusted to obtain a desired quality of an X-ray image. In particular, the relationship information may provide which arrangement range, i.e., an appropriate range of the arrangement status, is required for the user to obtain the desired quality. Therefore, the user may adjust a location of at least one of the X-ray radiator and the detection device so that the arrangement status is included in the arrangement range, i.e., an appropriate range. Accordingly, the user may consume less effort to exactly match the arrangement status of the X-ray radiator and the detection device. Therefore, the X-ray apparatus may have greatly improved user convenience. Furthermore, according to some exemplary embodiments, less time may be consumed for X-ray imaging. This is not only convenient for the user, but also, when an object of X-ray imaging is an animal or a human, convenient for the object.

The exemplary embodiments can be written as computer programs and can be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more exemplary embodiments have been described with reference to the figures, it will be understood by those of ordinary skill in the art that various changes in form and details may be made therein without departing from the spirit and scope as defined by the following claims.

What is claimed is:

1. An X-ray apparatus comprising:
   an X-ray radiator configured to radiate X-rays;
   a detection device comprising a grid configured to selectively transmit the X-rays radiated from the X-ray radiator and a detector configured to detect the X-rays transmitted through the grid;
   a controller configured to obtain:
      arrangement information that indicates an arrangement status of the X-ray radiator and the detection device, the arrangement status comprising an angular relationship and a distance relationship between the X-ray radiator and the detection device, and
      quality information that indicates a quality of an X-ray image, which corresponds to the arrangement status, wherein the X-ray image is obtained based on the detected X-rays selectively transmitted through the grid; and
   an output device configured to output the arrangement information and the quality information.

2. The X-ray apparatus of claim 1, wherein the output device further outputs relationship information that indicates qualities of an X-ray image, which respectively correspond to a plurality of arrangement ranges formable between the X-ray radiator and the detection device.

3. The X-ray apparatus of claim 2, wherein the arrangement information that is output from the output device indicates, on the relationship information, in which arrangement range from among the plurality of the arrangement ranges the arrangement status is comprised.

4. The X-ray apparatus of claim 2, wherein the output device outputs the relationship information such that the qualities of the X-ray image, which respectively correspond to the plurality of arrangement ranges, are distinguished from each other by using different colors.

5. The X-ray apparatus of claim 2, further comprising an input interface that receives, from a user, a command for setting or re-setting the relationship information,
   wherein the command for setting or re-setting the relationship information comprises at least one command selected from a command for setting or re-setting the plurality of arrangement ranges, a command for setting or re-setting the qualities of the X-ray image, which respectively correspond to the plurality of arrangement ranges, and a command for setting or re-setting colors that distinguishes the qualities of the X-ray image, which respectively correspond to the plurality of arrangement ranges, from each other.

6. The X-ray apparatus of claim 1, further comprising an input interface that receives, from a user, at least one command selected from an adjustment command for adjusting a location of at least one of the X-ray radiator and the detection device, and a radiation command for instructing the X-ray radiator to radiate X-rays,
   wherein the controller controls an operation of at least one of the X-ray radiator and the detection device based on the adjustment command or the radiation command.

7. The X-ray apparatus of claim 2, further comprising a memory that stores the relationship information.

8. The X-ray apparatus of claim 1, further comprising a location information acquirer that obtains location information of at least one of the X-ray radiator and the detection device,
   wherein the controller obtains the arrangement information based on the location information.

9. The X-ray apparatus of claim 1, wherein the arrangement information further comprises at least one information selected from angle information that indicates a degree of parallelness of the X-ray radiator and the detection device, centering information that indicates a degree of matching between a center of the X-ray radiator and a center of the detection device, and distance information about a distance between the X-ray radiator and the detection device.

10. A workstation comprising:
    a controller configured to obtain:
       arrangement information that indicates an arrangement status of an X-ray radiator of an X-ray apparatus and a detection device, the detection device comprising a grid configured to selectively transmit X-rays radiated from the X-ray radiator and a detector configured to detect the X-rays transmitted through the grid, the arrangement status comprising an angular relationship and a distance relationship between the X-ray radiator and the detection device, and
       quality information that indicates a quality of an X-ray image, which corresponds to the arrangement status, wherein the X-ray image is obtained based on the detected X-rays selectively transmitted through the grid; and
    an output device configured to output the arrangement information and the quality information.

11. The workstation of claim 10, wherein the output device further outputs relationship information that indicates qualities of an X-ray image, which respectively correspond to a plurality of arrangement ranges formable between the X-ray radiator and the detection device.

12. The workstation of claim 11, wherein the arrangement information that is output from the output device indicates, on the relationship information, in which arrangement range from among the plurality of the arrangement ranges the arrangement status is comprised.

13. The workstation of claim 11, wherein the output device outputs the relationship information such that the qualities of the X-ray image, which respectively correspond to the plurality of arrangement ranges, are distinguished from each other by using different colors.

14. The workstation of claim 11, further comprising an input interface that receives, from a user, a command for setting or re-setting the relationship information,
wherein the command for setting or re-setting the relationship information comprises at least one command selected from a command for setting or re-setting the plurality of arrangement ranges, a command for setting or re-setting the qualities of the X-ray image, which respectively correspond to the plurality of arrangement ranges, and a command for setting or re-setting colors that distinguishes the qualities of the X-ray image, which respectively correspond to the plurality of arrangement ranges, from each other.

15. The workstation of claim 10, further comprising an input interface that receives, from a user, at least one command selected from an adjustment command for adjusting a location of at least one of the X-ray radiator and the detection device and a radiation command for instructing the X-ray radiator to radiate X-rays,
wherein the controller controls an operation of at least one of the X-ray radiator and the detection device, based on the adjustment command or the radiation command.

16. A method of operating an X-ray system, the method comprising:
obtaining arrangement information that indicates an arrangement status of an X-ray radiator of an X-ray apparatus and a detection device;
obtaining quality information that indicates a quality of an X-ray image, which corresponds to the arrangement status; and
outputting the arrangement information and the quality information,
wherein the arrangement information comprises angle information that indicates a degree of parallelness of the X-ray radiator and the detection device, and
wherein the detection device comprises a grid configured to selectively transmit X-rays radiated from the X-ray radiator.

17. The method of claim 16, wherein the arrangement information and the quality information are output with relationship information that indicates qualities of an X-ray image, which respectively correspond to a plurality of arrangement ranges formable between the X-ray radiator and the detection device.

18. The method of claim 17, further comprising:
receiving, from a user, at least one command selected from an adjustment command for adjusting a location of at least one of the X-ray radiator and the detection device and a radiation command for instructing the X-ray radiator to radiate X-rays; and
controlling an operation of at least one of the X-ray radiator and the detection device, based on the adjustment command or the radiation command.

19. A non-transitory computer-readable recording medium having recorded thereon a program, which, when executed by at least one processor, is configured to cause the at least one processor to:
obtain arrangement information that indicates an arrangement status of an X-ray radiator of an X-ray apparatus and a detection device, the detection device comprising a grid configured to selectively transmit X-rays radiated from the X-ray radiator and a detector configured to detect the X-rays transmitted through the grid, the arrangement status comprises an angular relationship and a distance relationship between the X-ray radiator and the detection device;
obtain quality information that indicates a quality of an X-ray image, which corresponds to the arrangement status, wherein the X-ray image is obtained based on the detected X-rays selectively transmitted through the grid; and
output the arrangement information and the quality information.

* * * * *